United States Patent
Sewell

(10) Patent No.: US 12,236,167 B2
(45) Date of Patent: Feb. 25, 2025

(54) SYSTEM AND METHOD OF EMBODIED STRESS ANALYSIS

(71) Applicant: Gresham Smith, Nashville, TN (US)

(72) Inventor: Michael William Sewell, Louisville, KY (US)

(73) Assignee: Gresham Smith, Nashville, TN (US)

( * ) Notice: Subject to any disclaimer, the term of this patent is extended or adjusted under 35 U.S.C. 154(b) by 505 days.

(21) Appl. No.: 17/853,489

(22) Filed: Jun. 29, 2022

(65) Prior Publication Data

US 2022/0335173 A1 Oct. 20, 2022

Related U.S. Application Data

(63) Continuation-in-part of application No. 17/202,671, filed on Mar. 16, 2021, now Pat. No. 11,501,501.

(60) Provisional application No. 63/044,563, filed on Jun. 26, 2020.

(51) Int. Cl.
| | |
|---|---|
| *G06F 30/13* | (2020.01) |
| *A61B 5/00* | (2006.01) |
| *A61B 5/0205* | (2006.01) |
| *A61B 5/024* | (2006.01) |
| *A61B 5/11* | (2006.01) |
| *A61B 5/16* | (2006.01) |

(52) U.S. Cl.
CPC ............ *G06F 30/13* (2020.01); *A61B 5/0205* (2013.01); *A61B 5/1112* (2013.01); *A61B 5/165* (2013.01); *A61B 5/7225* (2013.01); *A61B 5/742* (2013.01); *A61B 5/024* (2013.01)

(58) Field of Classification Search
CPC ..... G06F 30/13; A61B 5/0205; A61B 5/1112; A61B 5/165; A61B 5/7225; A61B 5/742; A61B 5/024
See application file for complete search history.

(56) References Cited

U.S. PATENT DOCUMENTS

| | | |
|---|---|---|
| 6,599,243 B2 | 7/2003 | Woltermann et al. |
| 6,968,294 B2 | 11/2005 | Gutta et al. |
| 7,450,986 B2 | 11/2008 | Nguyen et al. |
| 7,830,249 B2 | 11/2010 | Dorneich et al. |
| 7,880,607 B2 | 2/2011 | Olson et al. |
| 8,157,730 B2 | 4/2012 | LeBoeuf et al. |
| 8,180,591 B2 | 5/2012 | Yuen et al. |

(Continued)

*Primary Examiner* — Jonathan T Kuo
(74) *Attorney, Agent, or Firm* — Spencer Fane LLP; Steven J. Laureanti

(57) ABSTRACT

A system and method are disclosed for measuring embodied stress relative to a location. The method comprises receiving stress data from sensors of monitoring devices, building a locational model from mapping data, receiving location data correlated with the stress data, filtering the stress data and the location data by comparing the location data to a locational model, aggregating the filtered stress data and the filtered location data into groups according to bins defined by a grid, analyzing the stress data and the location data to associate the stress data with the location data according to the locational model, generating a stress visualization based on the stress data and the location data; and deriving an emotion of one or more locations according to the locational model. The method further performs a locational sequence analysis by tracking stress changes along a sequence of locations to plan reductions of stress levels.

20 Claims, 15 Drawing Sheets

(56) References Cited

U.S. PATENT DOCUMENTS

| | | |
|---|---|---|
| 8,738,321 B2 | 5/2014 | Yuen et al. |
| 8,961,415 B2 | 2/2015 | LeBoeuf et al. |
| 9,519,755 B2 | 12/2016 | Saalasti et al. |
| 9,968,264 B2 | 5/2018 | Tzvieli et al. |
| 10,055,121 B2 | 8/2018 | Chaudri et al. |
| 10,076,250 B2 | 9/2018 | Tzvieli et al. |
| 10,136,856 B2 | 11/2018 | Tzvieli et al. |
| 10,534,900 B2 | 1/2020 | Cheong et al. |
| 10,578,456 B2 | 3/2020 | Huang |
| 10,595,730 B2 | 3/2020 | LeBoeuf et al. |
| 10,610,109 B2 | 4/2020 | Zhou |
| 10,729,324 B2 | 8/2020 | Gelissen et al. |
| 10,791,924 B2 | 10/2020 | Toth et al. |
| 10,867,218 B2 | 12/2020 | Gallagher et al. |
| 10,902,714 B2 | 1/2021 | Bergman et al. |
| 11,030,885 B2 | 6/2021 | Kime et al. |
| 11,138,503 B2 | 10/2021 | Wood et al. |
| 11,156,464 B2 | 10/2021 | Young et al. |
| 2006/0064277 A1 | 3/2006 | Jung et al. |
| 2015/0335288 A1 | 11/2015 | Toth et al. |
| 2017/0173262 A1 | 6/2017 | Veltz |
| 2018/0011978 A1 | 1/2018 | Reeckmann |
| 2018/0049675 A1* | 2/2018 | Kerber .................. A61B 5/1112 |
| 2020/0305791 A1 | 10/2020 | Wirth et al. |
| 2021/0038088 A1 | 2/2021 | Atallah et al. |
| 2022/0361788 A1* | 11/2022 | Shah ...................... G16H 50/20 |

* cited by examiner

SYSTEM AND METHOD OF EMBODIED STRESS ANALYSIS

CROSS-REFERENCE TO RELATED APPLICATIONS

This application is a continuation-in-part of U.S. patent application Ser. No. 17/202,671, filed on Mar. 16, 2021, entitled "BIOMETRIC FEEDBACK SYSTEM," which claims the benefit under 35 U.S.C. § 119(e) to U.S. Provisional Application No. 63/044,563, filed Jun. 26, 2020. U.S. patent application Ser. No. 17/202,671 and U.S. Provisional Application No. 63/044,563 are assigned to the assignee of the present application.

TECHNICAL FIELD

The present application relates to a system for measuring embodied stress of locations, and, in particular, to systems and methods of modeling and measuring embodied stress and locational sequences of stress in the design and re-design of architectural settings, public spaces, landscapes, and other environments.

BACKGROUND

In the design and re-design of buildings, roads, parks, and other features of the environment, community surveys, public forums, and vehicle crash and other data are often consulted in the design and re-design process. However, data gained from such perspectives may be biased. For example, public forums may be dominated by a few participants, and survey results can be skewed by survey design. Moreover, participants may not be able to articulate or even be aware of subtle causes of stress in the environment. The lack of an objective measure for providing input in the design and re-design process is undesirable.

BRIEF DESCRIPTION OF THE DRAWINGS

A more complete understanding of the present invention may be derived by referring to the detailed description when considered in connection with the following illustrative figures. In the figures, like reference numbers refer to like elements or acts throughout the figures.

DETAILED DESCRIPTION

Figure 1:
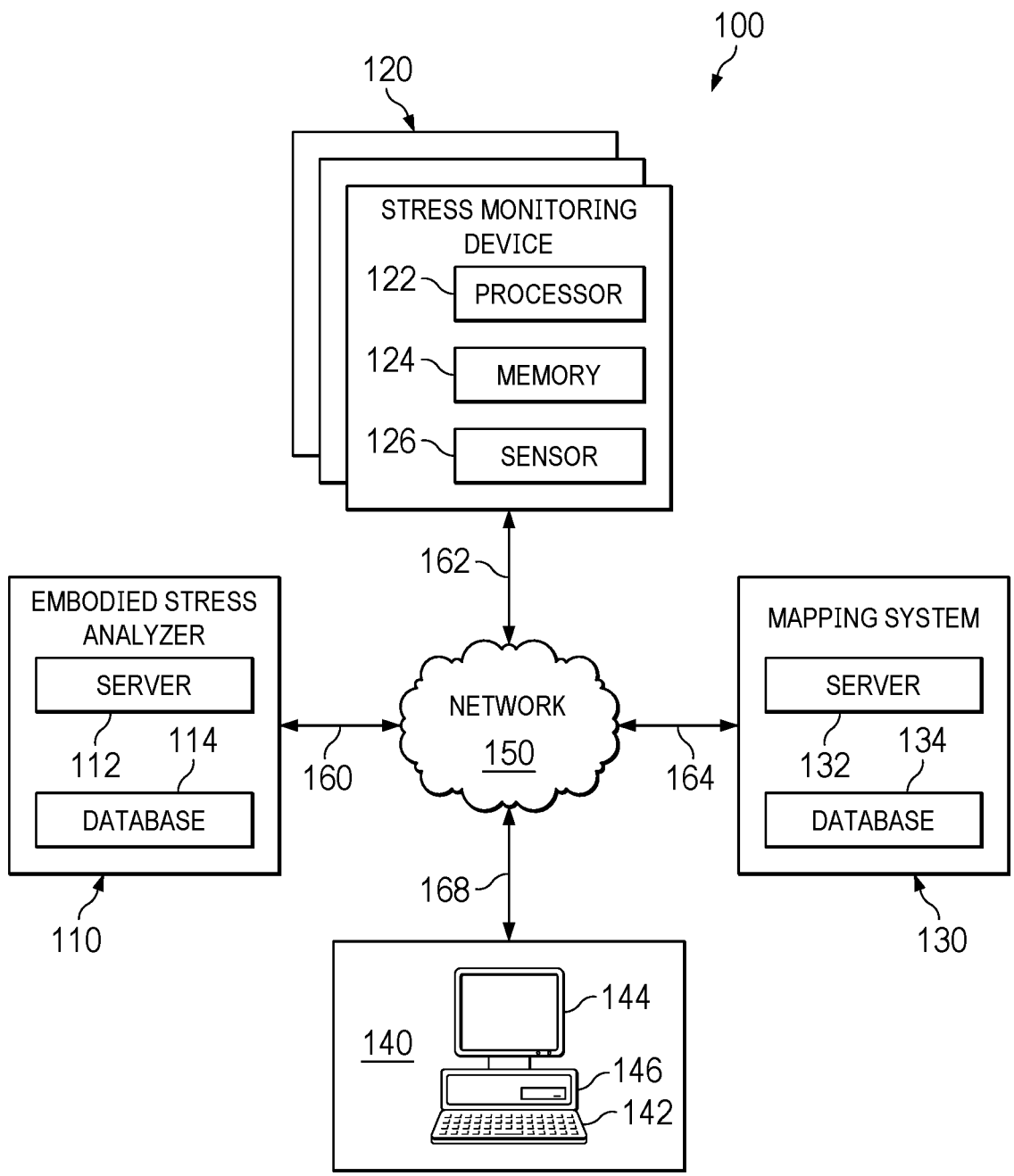
FIG. 1 illustrates an embodied stress analysis system, according to a first embodiment.

Systems and methods of the invention presented herein are described below in the drawings and detailed description. Unless specifically noted, it is intended that the words and phrases herein be given their plain, ordinary, and accustomed meaning to those of ordinary skill in the applicable arts.

In the following description, and for the purposes of explanation, numerous specific details are set forth in order to provide a thorough understanding of the various aspects of the invention. It will be understood, however, by those skilled in the relevant arts, that embodiments of the present invention may be practiced without these specific details. In other instances, known structures and devices are shown and/or discussed more generally in order to avoid obscuring the invention. In many cases, a description of the operation is sufficient to enable one of ordinary skill in the applicable art to implement the various forms of the invention. It should be appreciated that there are many different and alternative configurations, devices and technologies to which the disclosed inventions may be applied. The full scope of the present disclosure is not limited to the examples described below.

FIG. 1 illustrates embodied stress analysis system 100, according to a first embodiment. The system comprises embodied stress analyzer 110, one or more stress monitoring devices 120, mapping system 130, computer 140, network 150, and one or more communication links 160-168. Although a single embodied stress analyzer 110, one or more stress monitoring devices 120, a single mapping system 130, a single computer 140, and a single network 150 are shown and described, embodiments contemplate any number of embodied stress analyzers, stress monitoring devices, mapping systems, computers, and networks, according to particular needs. Although FIG. 1 illustrates embodied stress analyzer 110, one or more stress monitoring devices 120, mapping system 130, and computer 140 as distinct devices, in other embodiments the functions of embodied stress analyzer 110, one or more stress monitoring devices 120, mapping system 130, and computer 140 may be performed by a single computing device comprising a processor and memory, or networked cloud computing device comprising one or more networked processors and one or more networked memories.

In one embodiment, embodied stress analyzer 110 comprises server 112 and database 114. As described in more detail below, server 112 of embodied stress analyzer 110 comprises one or more modules to, for example, measure and calculate embodied stress of a place and the stress of a locational sequence through a location. Embodiments contemplate designing or altering locations to invoke optimal levels of stress (including, for example, a flow state) according to characteristics of the environment (e.g., crossing an intersection, a factory floor, handling of dangerous materials, environmental hazards, and the like) and according to particular needs.

One or more stress monitoring devices 120 are electronic devices comprising one or more processors 122, memory 124, one or more sensors 126, and may include any suitable input device, output device, fixed or removable computer-readable storage media, or the like. According to embodiments, one or more stress monitoring devices 120 comprise one or more electronic devices that measure stress or receive stress measurements from one or more sensors 126. Additionally, one or more sensors 126 of one or more stress monitoring devices 120 may be located at one or more locations local to, or remote from, the one or more stress monitoring devices 120, including, for example, one or more sensors 126 integrated into one or more stress monitoring devices 120 and/or one or more sensors 126 distantly located from one or more stress monitoring devices 120 and communicatively coupled to the one or more stress monitoring devices 120. Sensors 126 may include sensors coupled to wearable devices of one or more users and configured to detect biometrics and generate a digital signal that indicates, for example, heartbeat, perspiration, voice, eye movement, brain signals, EKG, position, movement, or orientations of body or body parts (including posture), respiration, temperature, and the like. Data received from the one or more sensors may be used to evaluate the current state (e.g., stress) of the user.

One or more stress monitoring devices 120 may comprise a wearable electronic device capable of monitoring and recording heart rate data or other biometric data. In other embodiments, one or more stress monitoring devices 120 may be an external location system, such as a radio frequency identification (RFID) system, a light detection and ranging (LIDAR) system, a radio detection and ranging (RADAR) system, or any other external system capable of remotely monitoring and recording heart rate data or other biometric data. In addition, or as an alternative, one or more stress monitoring devices 120 may comprise, or be communicatively coupled with, a networked communication device, such as, for example, a smartphone, a tablet computer, a wireless device, or the like. One or more stress monitoring devices 120 may generate a mapping of a recorded stress measurement (or other biometric) by tagging a location associated with a measurement. This may include, for example, a GPS module coupled with one or more stress monitoring devices 120 that records location data during measurement of the biometric or stress. Embodiments comprise, for example, a wearable electronic device comprising a heartrate monitor that records blood flow or electrical signals of the user and associates the measurements with movement and activity detection and may additionally include, for example, associating user identity data, location data, time data, demographics, and the like. As explained in more detail below, embodied stress analysis system 100 may use the measurements and associated data mappings to determine, for example, whether a user is oriented toward or away from a particular environmental structure or feature, rate of movement through a location, any waypoints or stops through a location, determination whether a movement or action is in conformity with expected or modeled sequences through an environmental location (e.g., posted directions or other modeled movement or activity in the environment), identify any amount of non-conformity with one or more modeled movements or activities, evaluate progress of movement or activity through a location, and the like.

According to embodiments, mapping system 130 comprises server 132 and database 134. According to embodiments, one or more modules of server 132 generates one or more mappings of one or more locations, and provides the one or more mappings to embodied stress analysist 110 for generating a locational model 222 (FIG. 2) on which to bin the biometrics measured by one or more stress monitoring devices 120. In one embodiment, mapping system 130 generates mappings of environments (e.g., building plans, maps of outdoor spaces, and the like). By way of example only and not by way of limitation, server 132 of one or more mapping systems 130 generates a building plan which is utilized by embodied stress analyst 110 to build locational model 222 comprising bins by assigning each bin to a room (or other architectural feature) indicated on the building plan received from mapping systems 130. In addition, or as an alternative, mapping system 120 comprises a commercial mapping service (e.g., GOOGLE MAPS commercial mapping service), which generates a map of an outdoor environment and which is then utilized by embodied stress analyst 110 to generate locational model 222, as described in further detail below.

As shown in FIG. 1, embodied stress analysis system 100 operates on one or more computers 140 that are integral to or separate from the hardware and/or software that support embodied stress analyzer 110, one or more stress monitoring devices 120, and mapping system 130. Embodied stress analysis system 100 comprising embodied stress analyzer 110, one or more stress monitoring devices 120, and mapping system 130 may operate on one or more computers 140 that are integral to or separate from the hardware and/or software that support embodied stress analyzer 110, one or more stress monitoring devices 120, and mapping system 130. One or more computers 140 may include any suitable input device 142, such as a keypad, mouse, touch screen, microphone, or other device to input information. One or more computers 140 may also include any suitable output device 144, such as, for example, a computer monitor, that may convey information associated with the operation of embodied stress analysis system 100, including digital or analog data, visual information, or audio information. Computer 140 may include fixed or removable computer-readable storage media, including a non-transitory computer readable medium, magnetic computer disks, flash drives, CD-ROM, in-memory device or other suitable media to receive output from and provide input to embodied stress analysis system 100.

Computer 140 may include one or more processors 146 and associated memory to execute instructions and manipulate information according to the operation of embodied stress analysis system 100 and any of the methods described herein. One or more processors 146 may execute an operating system program stored in memory to control the overall operation of computer 140. For example, one or more processors 146 control the reception and transmission of signals within the system. One or more processors 146 execute other processes and programs resident in memory, such as, for example, registration, identification, communication, and movement of data into or out of the memory, as required by an executing process. In addition, or as an alternative, embodiments contemplate executing the instructions on computer 140 that cause computer 140 to perform functions of the method. Further examples may also include articles of manufacture including tangible computer-readable media that have computer-readable instructions encoded thereon, and the instructions may comprise instructions to perform functions of the methods described herein.

In addition, embodied stress analysis system 100 may comprise a cloud-based computing system having processing and storage devices at one or more locations, local to, or remote from embodied stress analyzer 110, one or more stress monitoring devices 120, and mapping system 130. In addition, each of one or more computers 140 may be a work station, personal computer (PC), network computer, notebook computer, tablet, personal digital assistant (PDA), cell phone, telephone, smartphone, wireless data port, or any other suitable computing device. In an embodiment, one or more users may be associated with embodied stress analyzer 110, one or more stress monitoring devices 120, and mapping system 130.

In one embodiment, each of embodied stress analyzer 110, one or more stress monitoring devices 120, mapping system 130, and computer 140 may be coupled with network 150 using communication links 160-166, which may be any wireline, wireless, or other link suitable to support data communications between embodied stress analyzer 110 and network 150 during operation of embodied stress analysis system 100. Although communication links 160-166 are shown as generally coupling embodied stress analyzer 110, one or more stress monitoring devices 120, mapping system 130, and computer 140 to network 150, any of embodied stress analyzer 110, one or more stress monitoring devices 120, mapping system 130, and computer 140 may communicate directly with each other, according to particular needs.

In another embodiment, network 150 includes the Internet and any appropriate local area networks (LANs), metropolitan area networks (MANs), or wide area networks (WANs) coupling embodied stress analyzer 110, one or more stress monitoring devices 120, mapping system 130, and computer 140. For example, data may be maintained locally to, or externally of embodied stress analyzer 110, one or more stress monitoring devices 120, mapping system 130, and computer 140 and made available to one or more associated users of embodied stress analyzer 110, one or more stress monitoring devices 120, mapping system 130, and computer 140 using network 150 or in any other appropriate manner. For example, data may be maintained in a cloud database at one or more locations external to embodied stress analyzer 110, one or more stress monitoring devices 120, mapping system 130, and computer 140 and made available to one or more associated users of embodied stress analyzer 110, one or more stress monitoring devices 120, mapping system 130, and computer 140 using the cloud or in any other appropriate manner. Those skilled in the art will recognize that the complete structure and operation of network 150 and other components within embodied stress analysis system 100 are not depicted or described. Embodiments may be employed in conjunction with known communications networks and other components.

Figure 2:
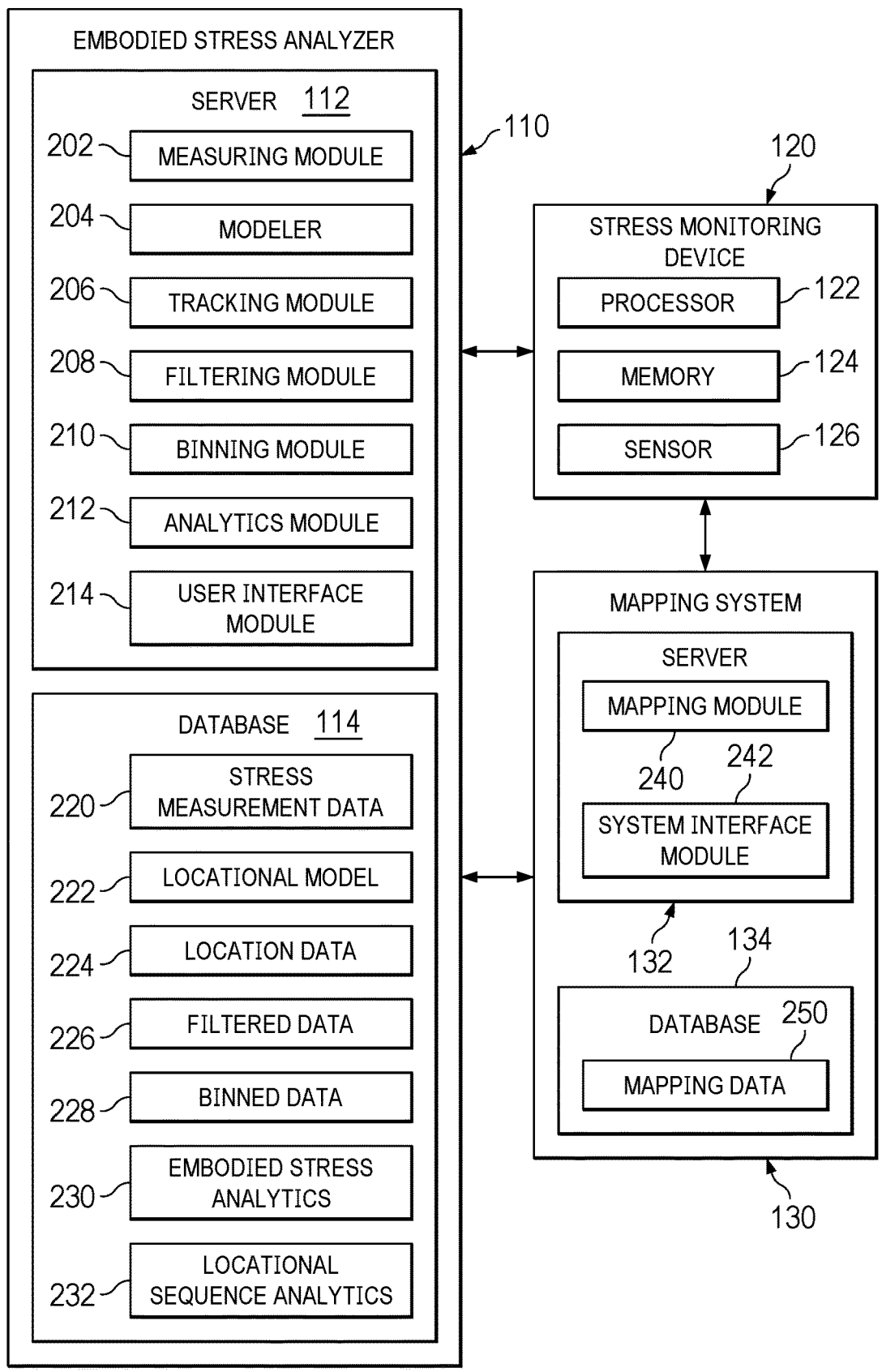
FIG. 2 illustrates the embodied stress analyzer, stress monitoring device, and mapping system of the embodied stress analysis system of FIG. 1 in greater detail, according to an embodiment.

FIG. 2 illustrates embodied stress analyzer 110, stress monitoring device 120, and mapping system 130 of embodied stress analysis system 100 of FIG. 1 in greater detail, according to an embodiment. As disclosed above, embodied stress analyzer 110 comprises server 112 and database 114. Although embodied stress analyzer 110 is shown as comprising single server 112 and single database 114, embodiments contemplate any suitable number of servers 112 or databases 114 internal to or externally coupled with embodied stress analyzer 110.

Server 112 of embodied stress analyzer 110 may comprise measuring module 202, modeler 204, tracking module 206, filtering module 208, binning module 210, analytics module 212, and user interface module 214. Although server 112 is illustrated and described as comprising a single measuring module 202, modeler 204, tracking module 206, filtering module 208, binning module 210, analytics module 212, and user interface module 214, embodiments contemplate any suitable number or combination of these located at one or more locations, local to, or remote from embodied stress analyzer 110, such as on multiple servers 112 or computers 140 at any location in embodied stress analysis system 100.

Measuring module 202 stores stress monitoring data received from one or more stress monitoring devices 120 in database 112. According to embodiments, measuring module 202 receives biometric data from stress monitoring devices and stores the biometric data as stress measurement data 220 and associates the stress measurement data 220 with any associated location data 224, demographics, roles, user identity, movement, or other like data associated with the stress measurements, as described in further detail herein. Modeler 204 of embodied stress analyzer 110 builds locational model 222. According to embodiments, modeler 204 builds locational model 222, which is used by binning module 210 to calculate the embodied stress of a location. In an embodiment, modeler 204 is utilized by user interface module 214 to build a model of an environment using user-interactive visual elements to define locations associated with an environment, place, building plan, map, and the like, as described in further detail below.

Tracking module 206 stores location data received from either one or more wearable stress monitoring devices 120 in database 112 or an external location system that can be corroborated to user stress data. According to embodiments, tracking module 206 receives location information from stress monitoring devices and stores the location data as location data 224 and associates location data 224 with any associated stress measurement data 220, demographics, roles, user identity, movement, or other like data associated with the location information, as described in further detail herein. In addition, or as an alternative, location data is received from an RFID system or other Real-Time Location System (RTLS).

Filtering module 208 sorts, modifies, and cleans measurement data 220 and location data 224 to generate filtered data 226. According to one embodiment, filtering module 208 cleans measurement data 220. In addition or as an alternative, filtering module 208 sorts measurement data 220 and location data 224 according to one or more of user-selected metrics, which may include, but are not limited to: planned usage of a place or environment, role of user within the location, movement of a user within the location, and the like. By way of example only and not by way of limitation, role-based filtering may comprise filtering measurement data 220 for a hospital embodied stress analysis differently based on stress measurements received from one or more stress monitoring devices 120 associated with doctors versus measurements from one or more stress monitoring devices 120 associated with nurses, patients, visitors, and the like. By way of an additional, non-limiting example, filtering module 208 filters measurement data 220 according to movements associated with measurements, such as, for example, movement in a particular direction (e.g., with traffic, against traffic, entering a room, exiting a room, passing through a particular passageway or path between locations, and the like). According to embodiments, one or more stress monitoring devices 120 detect movements, directions, predicted activities and the like with stress and biometric measurements, which are stored with measurement data 220.

Binning module 210 generates binned data 228 based, at least in part, defined locations within locational model 222.

In one embodiment, binning module 220 generates bins of aggregated stress scores for each location (e.g., area, space, landmark, environment, and the like) to be analyzed. Bin allocation by binning module 210 may be user-defined as based, at least in part, on the type of analysis to be performed, such as, for example, an analyst comprising a hospital administrator may bin rooms of a hospital that have similar designs and function, an analyst comprising an architect may bin rooms that have specific architectural features, an analyst comprising an engineers in charge of designing a roadway may bin data by the various functions of the roadway and adjacent properties (sidewalk, bike path, vehicular lane, green space, and the like), and the like. By way of an additional, non-limiting example, bin allocation by binning module 210 may be user-defined as based, at least in part, on the type of setting, such as, for example, a setting comprising a hockey arena whose sections may be binned based on expected interactions with other users, groups of users (checked by another player, crowd participants pounding the glass, and the like), and any number of stimuli happening at the venue (lighting, music, event happenings, etc.) and the like.

Analytics module 212 generates embodied stress analytics 230 and locational sequence analytics 232. Analytics module 212 generates stress analytics 230 and locational sequence analytics 232 which are utilized by user interface module 214 to display visualizations of stress embodied in a place or of a locational sequence, as described in further detail below. User interface module 214 of embodied stress analyzer 110 generates and displays a user interface (UI), such as, for an example, a graphical user interface (GUI), that displays one or more interactive visualizations identifying and quantifying embodied stress analytics 230 and locational sequence analytics 232. According to embodiments, user interface module 214 displays a GUI comprising interactive graphical elements for selecting locations of locational model 222 for binning, selecting and applying various filters to selected sets of data from measurement data 220, and, in response to (and based at least in part on) the selection, displaying one or more graphical elements identifying embodied stress, biometrics, and other data and analytics, as disclosed herein.

Database 114 of embodied stress analyzer 110 may comprise one or more databases or other data storage arrangements at one or more locations, local to, or remote from, server 112. Database 114 may comprise, for example, stress measurement data 220, locational model 222, location data 224, filtered data 226, binned data 228, embodied stress analytics 230, and locational sequence analytics 232. Although database 114 is shown and described as comprising stress measurement data 220, locational model 222, location data 224, filtered data 226, binned data 228, embodied stress analytics 230, and locational sequence analytics 232, embodiments contemplate any suitable number or combination of these, located at one or more locations, local to, or remote from, embodied stress analyzer 110 according to particular needs.

Stress measurement data 220 may comprise stress measurements using one or more sensors 136 of one or more stress monitoring devices 120. According to embodiments, stress measurement data 220 comprises biometric data from one or more stress monitoring devices 120, stress calculations, and/or any associated location data 224, demographics, roles, user identity, movement, or other like data associated with the stress measurements, as described in further detail herein.

Locational model 222 comprises a digital model of the embodied location for which stress is determined. According to one embodiment, locational model 222 is built over a map or architectural plan of locations. By way of example only and not by way of limitation, locational model 222 may represent indoor locations of a building, outdoor environment, and the like.

Location data 22 comprises data associating stress measurements with a physical location. Location data 224 may comprise, for example, GPS, cell tower triangulation, Bluetooth, coordinates, distance from a beacon, waypoint, environmental feature, or the like. Filtered data 226 comprises measurement data 220 and/or location data 224 filtered by filtering module 208. According to embodiments, filtered data 226 comprises sorted and/or cleaned data modified according to one or more filters, as disclosed herein.

Binned data 228 comprises measurement data 220, location data 224, and/or filtered data 226 assigned to a location of locational model 222. According to embodiments, binned data 228 is organized according to locations defined in the locational model 222 set by embodied stress analyzer 110. By way of example only, and not by way of limitation, embodied stress analyzer 110 establishes limits on where the emotional response of place exists, such as, for example, a room of a building, a location along a roadway, or other types of interior and exterior environments.

Figure 4:
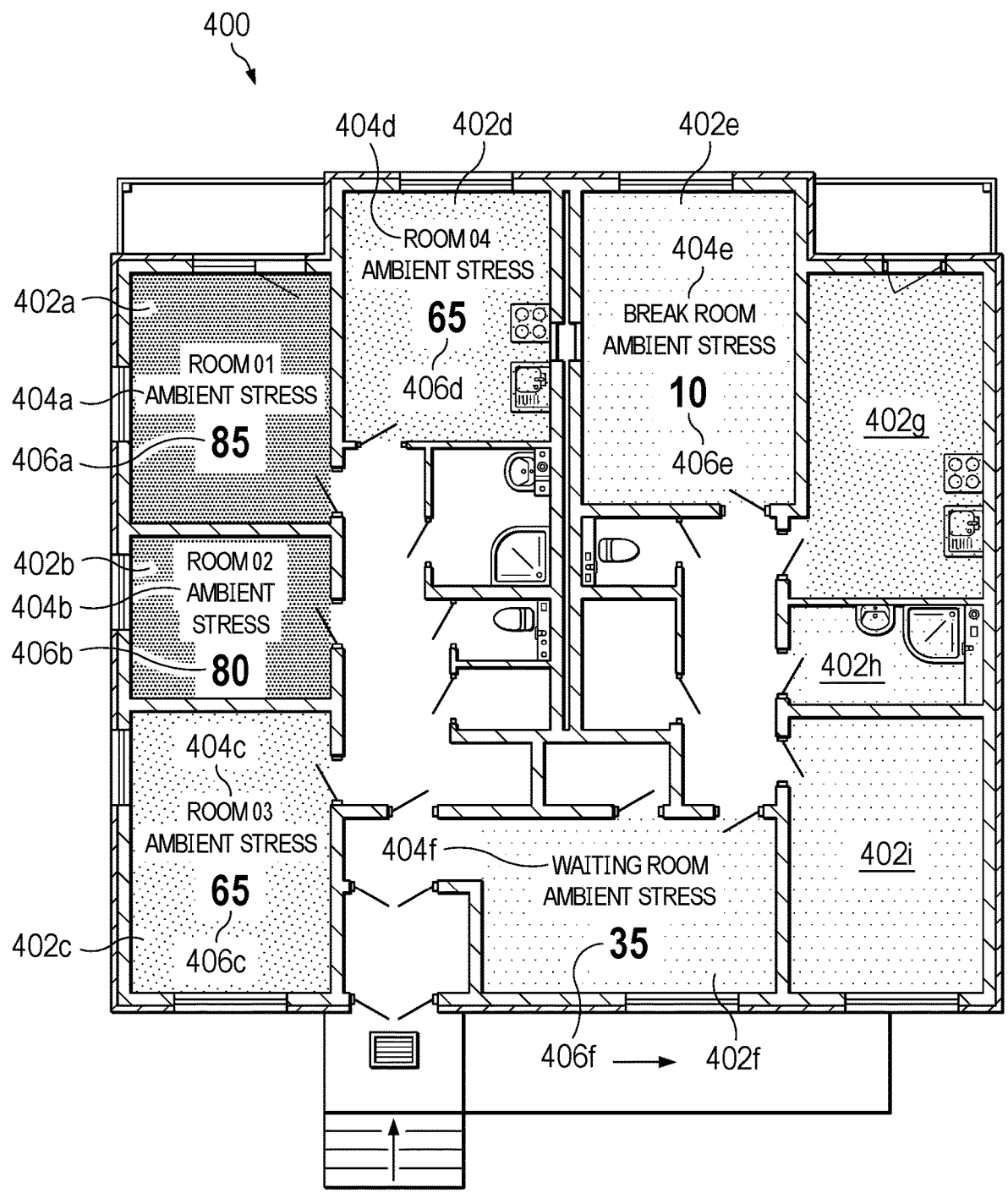
FIG. 4 illustrates embodied stress analysis visualization, according to an embodiment.

Embodied stress analytics 230 comprises stress scores and biometric calculations based, at least in part, on embodied stress of an interior or exterior environment, as described in further detail with embodied stress visualization 400 of FIG. 4. Locational sequence analytics 232 comprises stress scores and biometric calculations based, at least in part, on embodied stress of an interior or exterior environment along a locational sequence, as described in further detail with locational sequence stress visualization 500 of FIG. 5.

As disclosed above, stress monitoring device 120 comprises processor 122, memory 124, and sensor 126. According to embodiments, embodied stress analyzer 110 assigns autonomic stress to locations by tracking movement of one or more subjects wearing a one or more stress monitoring devices 120 comprising sensor 126 configured to measure biometric data and a location tracker (e.g., GPS tracker, indoor positioning system or other location-based techniques) configured to track location of measured biometrics. Sensor 126 may measure one or more biometrics (such as, for example, one or more of heart rate, heart rate variability, blood pressure, oxygenation, galvanic response, facial sentiment analysis, and the like). As disclosed in further detail below, biometric data from sensor 126 comprises subject changes to heart rate calculated using an algorithm and based, at least in part, on heart rate variability, rapidity of change, heart rate fluctuations. In one embodiment, sharp increases or decreases in heart rate fluctuations indicate stress and lower fluctuations combined with lower heart rate, comfort. Accordingly, stress may be measured according to improvements or decline of heart rate fluctuations, and embodied stress analyzer 110 may determine alterations to the environment based, at least in part, on stress measurements. Embodiments contemplate pooling many measurements of stress from the same, or different, one or more stress monitoring devices 120 and/or aggregating measurements from all locations within a predetermined or calculated distance from a particular location (i.e., all locations within one foot, five feet, ten feet, or any other distance, according to particular needs). In addition or as an alternative, location-correlated, biometric measurements received from one or more stress monitoring devices 120 may be augmented by other information development techniques, such as, for example, surveys, interviews, observation, traffic data, and the like.

As disclosed above, mapping system 130 comprises server 132 and database 134. Although mapping system 130 is shown as comprising single server 132 and single database 134, embodiments contemplate any suitable number of servers 132 or databases 134 internal to or externally coupled with mapping system 130.

Server 132 of mapping system 130 comprises mapping module 240 and system interface module 242. Although server 132 is illustrated and described as comprising a single mapping module 240 and a single system interface module 242, embodiments contemplate any suitable number or combination of these located at one or more locations, local to, or remote from mapping system 130, such as on multiple servers 132 or computers 140 at any location in embodied stress analysis system 100.

Mapping module 240 receives the physical location of one or more stress monitoring devices 120 from location data 224, identifies one or more environments (e.g., building plans, maps of outdoor locations, and the like) stored in mapping data 250 that correspond to the received physical locations, generates mappings comprising the corresponding environments, and transmits the generated mappings to embodied stress analyzer 110. In addition, or as an alternative, mapping module comprises an application server that transmits mapping data 250 to embodied stress analyzer 110.

System interface module 242 comprises an API that transmits mapping data 250 between embodied stress analyzer 110, one or more stress monitoring devices 120, and mapping system 130. According to embodiments, system interface module 242 transmits and receives electronic communication with any number of external sources of data.

Database 134 of mapping system 130 comprises mapping data 250. Although database 134 is shown and described as comprising mapping data 250, embodiments contemplate any suitable number or combination of data, located at one or more locations, local to, or remote from, embodied stress analyzer 110 according to particular needs.

Mapping data 250 comprises any number of blueprints, plans, building plans, architectural layouts, maps, or other layout of an indoor or outdoor environment.

Figure 3:
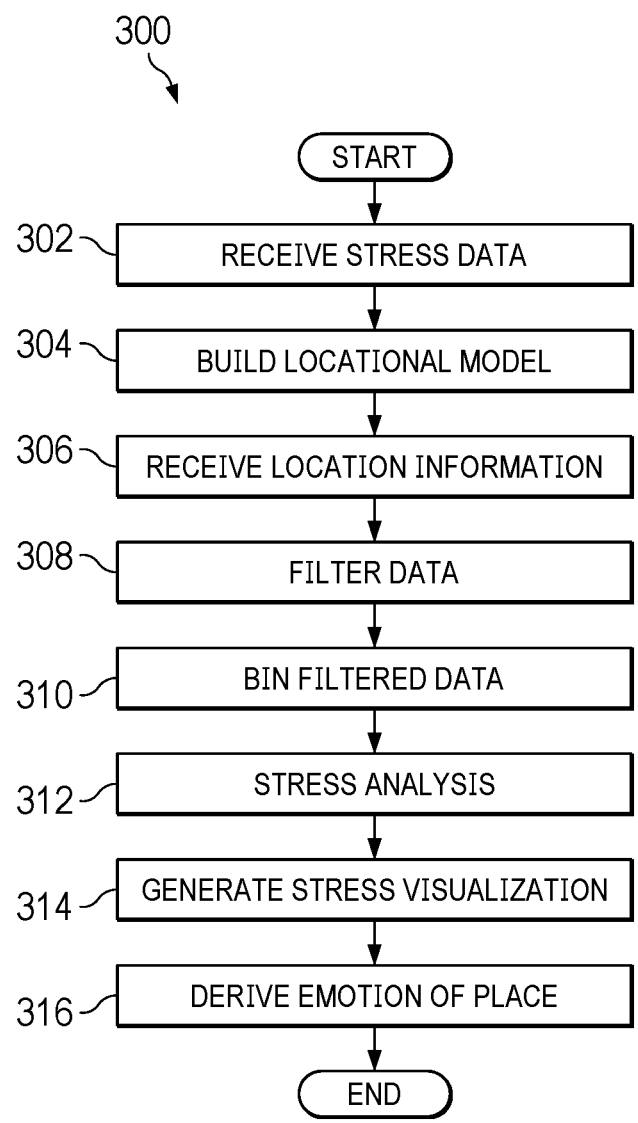
FIG. 3 illustrates the embodied stress analysis method, according to an embodiment.

FIG. 3 illustrates embodied stress analysis method 300, according to an embodiment. Embodied stress analysis method 300 proceeds by one or more activities, which although described in a particular order may be performed in one or more permutations, combinations, orders, or repetitions, according to particular needs.

At activity 302, measuring module 202 receives stress data from sensor 126 of one or more stress monitoring devices 120. As an example, one or more users within a particular location may each be wearing one or more stress monitoring devices 120 while moving through (such as working in) the location. The one or more stress monitoring devices 120 monitor and record heart rate information for the one or more users while they move through the location. In other embodiments, the one or more users may have their heart rate and other biometric information monitored and recorded using an external location system, such as an RFID, a LIDAR or a RADAR system.

At activity 304, modeler 204 builds locational model 222 from mapping data 250. Locational model 222 comprises a model of the location based on data defining the dimensions of the location as well as any subdivision (such as rooms) of the location. For example, if the location is a hospital, locational model 222 may include floors of the hospital, and rooms present on those floors, indicating entries and exists from those rooms as well as paths from one floor to another (such as stairs or an elevator).

At activity 306, tracking module 206 receives location information for one or more stress monitoring devices 120. For example, the location information received form the one or more stress monitoring devices may include a sub-location (such as a room) within the location that the one or more users wearing one or more stress monitoring devices 120 has passed through, or is currently in.

At activity 308, filtering module 208 filters stress measurement data 220 and location data 224. Stress management data 220 and location data 224 are filtered by comparing location data 224 within to locational model 222 to see if it should be applied within the bounds of an existing project associated with locational model 222, or stored in a general, worldview for locational model 222. The data is further filtered to eliminate any anomalies that would prevent the calculation of stress based on our algorithm, such as read errors recorded by one or more stress monitoring devices 120.

At activity 310, binning module 210 bins filtered data 226 to create binned data 228. Once stress management data 220 and location data 224 have been assigned to a project or view, the data is binned by comparing all points that fall within the confines of a user defined grid that covers the project limits within locational model 222. The user defined grid is a scalable variable that allows a user of embodied stress analyzer 110 to change the view of binned data 228 in real-time.

At activity 312, analytics module 212 performs analytics on binned data 228. As discussed in further detail above, binned data 228 is analyzed through one of several techniques to determine various levels of stress, such as a minimum stress, an average stress, a maximum stress, stress percentiles, etc. The result of this analysis is an embodied stress of the location corresponding to locational model 222. For example, certain rooms of the location may be indicating as "high stress" or "low stress" areas of the location.

At activity 314, user interface module 214 generates visualizations comprising embodied stress analytics 230 and/or locational sequence analytics 232. A formal visualization is developed using the embodied stress of the location. For example, if the location is a floor with rooms, the formal visualization may include a color-coded visualization of a floor-map, with certain colors indicating high stress areas of the floor and other colors indicating low stress areas of the floor.

At activity 316, embodied stress analyzer 110 derives an emotion of place for the location modeled by locational model 222. The emotion of place may be derived by reference to the embodied stress of the location determined at activity 312. For example, a low stress area or room may be determined to have a "calm" emotion of place while a high stress area or room may be determined to have a "stressful" or "focused" emotion of place. Continuing this example an area or room located between high stress and low stress areas may be determined to have a "recovery" or "ramp-up" emotion of place depending on if traffic is more commonly from the high stress area to the low stress area (a recovery space) or if traffic is more commonly from the low stress area to the high stress area (a ramp-up space).

FIG. 4 illustrates embodied stress analysis visualization 400, according to an embodiment. Embodied stress analysis visualization 400 comprises modeled locations 402a-402i, location labels 404a-404f, and location stress scores 406a-406f. As disclosed above, locational model 222 comprises a computer-modeled environment that may be based, at least in part, on a map, building plan, or other model of an environment. In this illustrated example of the embodied stress analysis visualization 400, modeled locations 402a-402i comprise rooms in a building modeled over a building plan. In this example, each of modeled locations 402a-402i comprise a room of the modeled building. Modeled locations 402a-402i may be associated with location labels 404a-404f indicating a name or key to stress scores 406a-406f associated with the modeled locations 402a-402i. According to embodiments, modeled locations 402a-402i comprise stress scores 406a-406f and/or are displayed using different patterns, colors, or visual elements to indicate the embodied stress of modeled locations 402a-402i.

According to embodiments, stress scores 406a-406f of modeled locations 402a-402f are calculated by first aggregating collected individual stress scores, binning the data based on specific location data and locational boundary conditions (in this case a room), and then data is normalized across all collected, binned data to come up with a unique score for a locationally bound place. The visualization can include numeric score of binned stress conditions, or color coded to easily derive visual representations of stress data.

In one embodiment, binning comprises aggregating measurements attributable to a modeled locations 402a-402i. By way of example only and not by way of limitation, modeled locations 402a-402i comprises a grid overlaid on a building plan, wherein particular coordinates on the grid are associated with a particular modeled location. When data is binned to a particular modeled location 402a-402i by falling within the modeled location on the grid, the stress measurement is attributed to the physical location represented by the modeled location. As disclosed above, embodiments contemplate one or more of measurement data 220, location data 224, and filtered data 226 assigned to a particular modeled location 402a-402i based, at least in part, on a distance from a particular environmental feature of the analyzed environment. By way of example only, and not by way of limitation, data assigned to a particular modeled location 402a-402i of embodied stress visualization 400 may comprise all data located within a particular room or within a particular distance from a modeled environmental feature.

For an outdoor location mapped to locational model 222 comprising a grid the location of exhibited stress may be binned to all measurements within a particular distance from a coordinate of the grid, such as, for example, one foot, five feet, ten feet, or any other distance, according to particular needs.

For an indoor environment mapped to locational model 222 comprising a building plan, the location of exhibited stress is binned according to the walls of a room or other type of architectural feature. For the indoor environment of embodied stress visualization 400, the grid of the locational model may not comprise each room corresponding to modeled locations 402a-402i is a grid cell. According to embodiments, bounds of a bin are defined by architectural features (such as, for example, walls or other types of architectural edges (e.g., the edge of a sidewalk or the bounds of a cubicle in an open work environment). In addition, or as an alternative, bounds of bins comprise a mathematical abstraction such as, for example, a grid overlay with cells assigned to one or more bins. Embodiments contemplate cells having the same, or different, geometric shapes, which may be user-defined and/or statistically calculated, according to particular needs.

Figure 5:
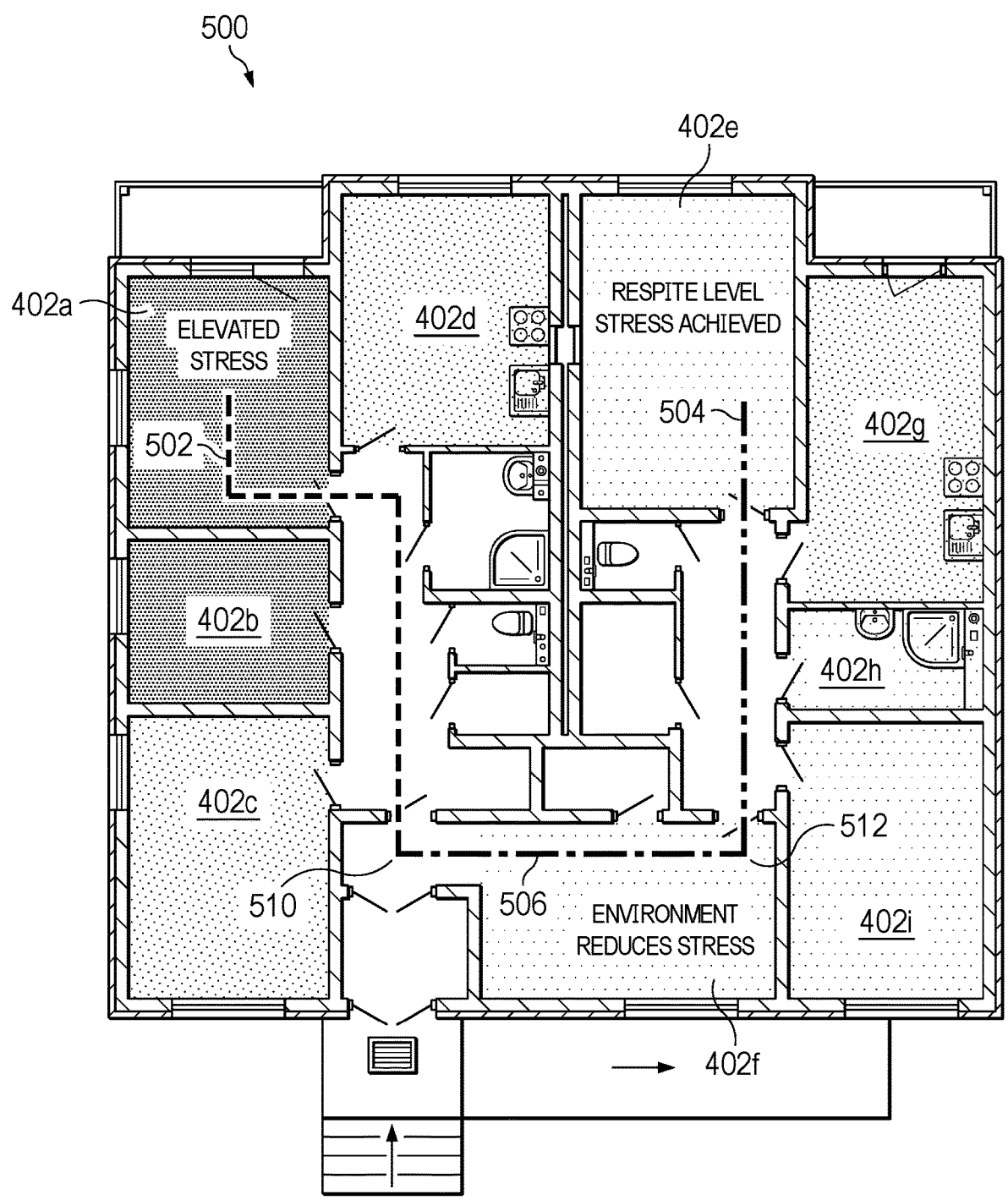
FIG. 5 illustrates locational sequence analysis visualization, according to an embodiment.

FIG. 5 illustrates locational sequence analysis visualization 500, according to an embodiment. As disclosed above, embodied stress of a location creates an ambient stress level which elicits stress responses in users of the location. Using locational sequence analysis, embodied stress analyzer 110 calculates the stress embodied in a sequence of locations that elicits a similar stress trend in end users and generates locational sequence analysis visualization 500. Locational sequence analysis visualization 500 provides for planning a sequence of locations that elicits specific stress outcomes in end users, such as, for example, determining how various routings through locations may have a positive or negative effect on a user of the location.

By way of example and not by way of limitation, locational sequence analysis visualization 500 of the illustrated embodiment comprises various modeled locations 402a-402i that comprise embodied stress, which may be measured according to embodied stress scores 404a-404f. After determining an ambient level of stress, the embodied stress per location, locational model 222 provides for creating locational sequence through particular locations. By varying the sequence and timing of locations along a locational sequence, the locational sequence analysis provides for planning a sequence that causes reduction (locational sequence 502), reduction (locational sequence 504) and/or maintenance (locational sequence 506) of a stress level, according to particular needs. Embodiments contemplate using locational sequence analysis to determine when a respite area is needed or determining if a particular one or more of modeled locations 402a-402i is a respite along a locational sequence.

Locational sequence analysis comprises locational sequences 502-506. Locational sequences 502-506 may be user defined in modeler 204 and/or based, at least in part, on location data 224 of users as they move through locations. By way of further non-limiting example, embodied stress analyzer 110 may generate locational sequences 502-506 by modeling through locational model 222, and the locational sequence analysis may generate a predicted trend along each of the one or more locational sequences 502-506 based on the differences in the measurements of the embodied stress of the locations along its length. For example, moving from a first modeled location 402a with a high level of stress, along locational sequence 502 comprising a neutral embodied stress (hallway) indicated by waypoint 510 may comprise a high-level of stress along locational sequence 502. Moving from waypoint 510 in hallway to modeled location 402f with a low level of embodied stress along locational sequence 506 may be associated with a neutral level of stress, and moving along locational sequence 504 from waypoint 512 in a low-stress modeled location 402f to another low-stress modeled location 402e is associated in this example with a low level of stress. Continuing with the illustrated example, based on the locational sequence analysis visualization 500, modeled location 402a is identified as an elevated stress environment, modeled location 402f is identified as an environment that reduces stress, and modeled location 402e is identified as a location where a respite-level of stress is achieved. By utilizing the locational sequence analysis, the stress response along locational sequences 502-506 may be calculated along with determining the amount of change in embodied stress of modeled locations 402a-402i (such as, for example, whether one or more of modeled locations 402a-402i is a recovery or respite location). In addition, or as an alternative, one or more locational sequences 502-506 may be associated with a travel time or average speed of travel which modify the amount of stress added to (or subtracted from) one or more locational sequences 502-506. In addition, waypoints 510-

512 may be added to one or more locational sequences 502-506 so that less time spent in a high stress location or more time spent in a low stress location are factored into locational sequence analysis, and differences in travel times between and through a location can be factored into the model of the analysis.

By way of example only and not by way of limitation, locational sequence analysis is utilized in the design of a building, such as, for example, For instance if we monitor stress and derive emotional response for a room used for a highly stressful function and then route that user to a room used for respite, we can trigger lighting or sound interventions that may yield a better individual user response.

In addition, or as an alternative, locational sequence analysis includes outdoor environments, such as, for example, streets, parks, and the like, as disclosed in further detail below.

Figure 6:
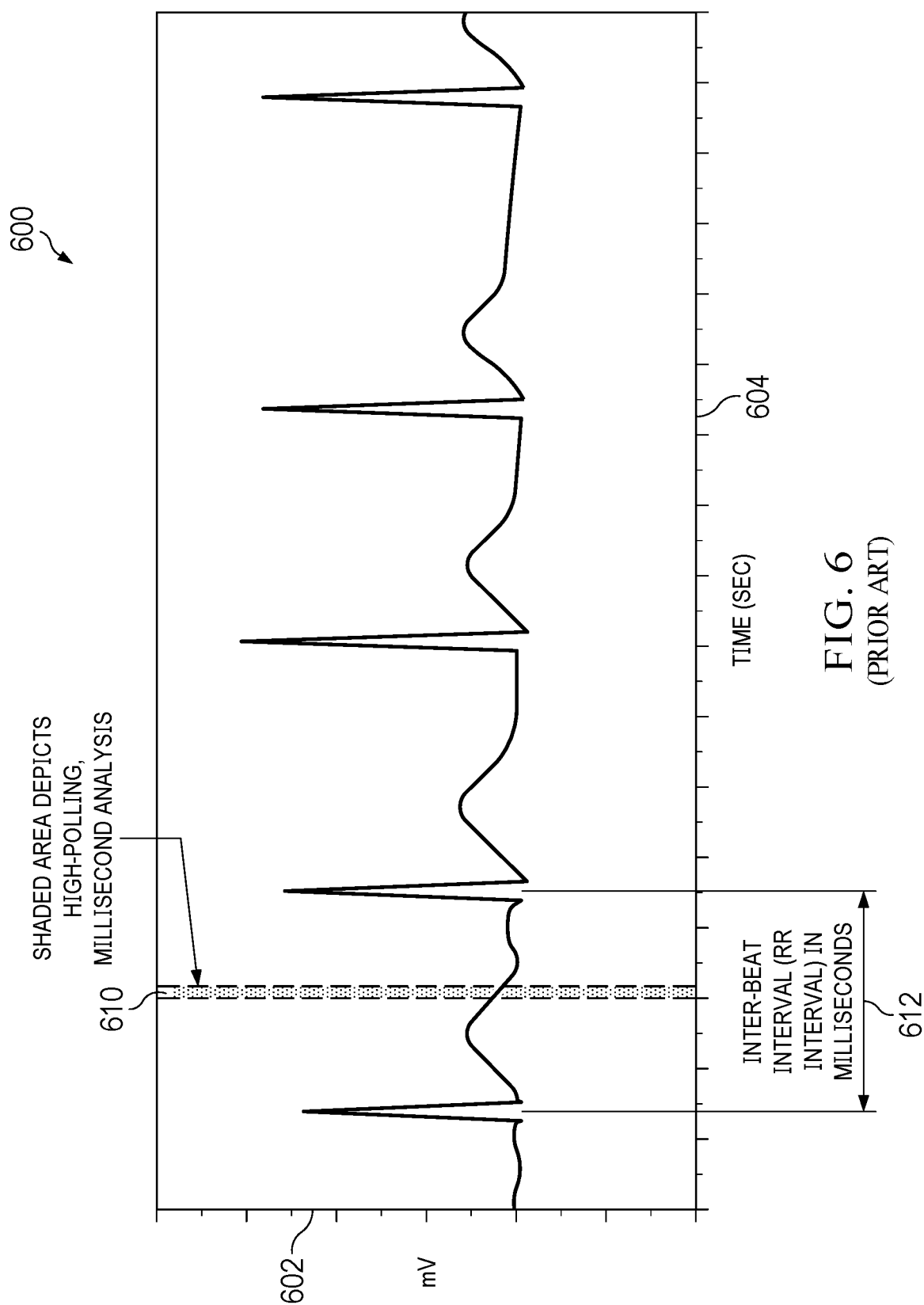
FIG. 6 illustrates a high-polling heartrate stress analysis chart, such as may be used in existing heartbeat tracking technology.

FIG. 6 illustrates high-polling heartrate stress analysis chart 600, such as from an existing heartrate monitoring system. High-polling heartrate stress analysis chart 600 comprises heartbeat 602 (y-axis, millivolt) of a heartbeat over time 604 (x-axis, seconds). Shaded area 610 indicates a high-polling, millisecond analysis, and distance 612 indicates the inter-beat interval (RR interval), which is typically expressed in terms of milliseconds.

Typically, in existing high-polling heartrate stress analysis systems, measurements of stress are based, at least in part, on a calculation relying on autonomic stress from EKG-level data, measuring inter-beat intervals to calculate stress response. Modern wearables (such as, for example, a FITBIT® wearable health monitor, APPLE WATCH® electronic internet-connected watch, and the like) may provide for short burst recording of EKG-level heartrate data to determine a snapshot of stress over a brief amount of time (typically thirty seconds worth of data or less). However, battery life limitations of such wearables allow only for the recording of heartbeat data in short intervals. Existing high-polling heartrate stress analysis systems will poll for heartrate data several times in a single second, which consumes significant battery life for a wearable device. For example, high-polling heartrate stress analysis chart 600 shows a single polling event for heartbeat data, which takes place within two heartbeats. Existing high polling heartrate stress analysis systems thus cannot accurately track heartbeat data over a longer interval, such as the time it may take to walk from one area of a building to another.

Figure 7:
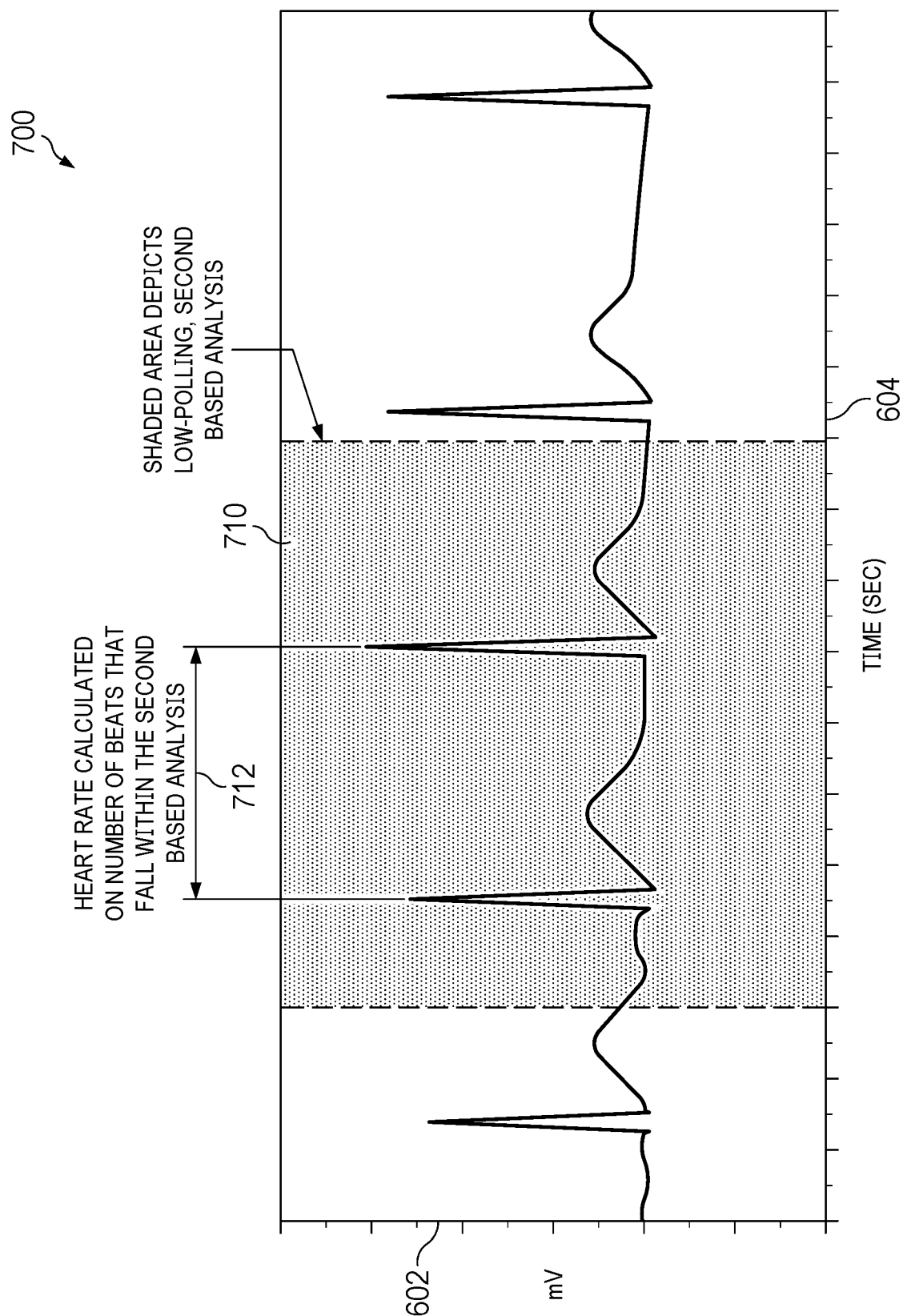
FIG. 7 illustrates a low-polling heartrate stress analysis chart, according to an embodiment.

FIG. 7 illustrates low-polling heartrate stress analysis chart 700, according to an embodiment. Low-polling heartrate stress analysis chart 700 comprises heartbeat 602 (y-axis, millivolt) of a heartbeat over time 604 (x-axis, seconds). Shaded area 710 indicates a low-polling, second-based analysis, and distance 712 indicates a heartrate calculation based on the number of beats that fall within a second-based time period. In an embodiment, stress monitoring device 120 utilizes an empathic algorithm, which uses low-polling (e.g., one-second interval recordings) heartrate trends to establish reliable stress response over longer periods of time than high-polling heartrate measurements used by existing heartbeat stress analysis systems. The empathic algorithm is based, at least in part, on slope analysis and rate of change comparison of heartrate. The empathic algorithm provides for more accessible stress data calculation with a fraction of device battery life, which allows for heartbeat data to be tracked over longer intervals compared to existing wearable heartbeat tracking technology. The empathic algorithm may be used to calculate various heart rate variability metrics based on heart rate variability, rapidity of change, heart rate fluctuations or other heart rate variability metrics.

Figure 8:
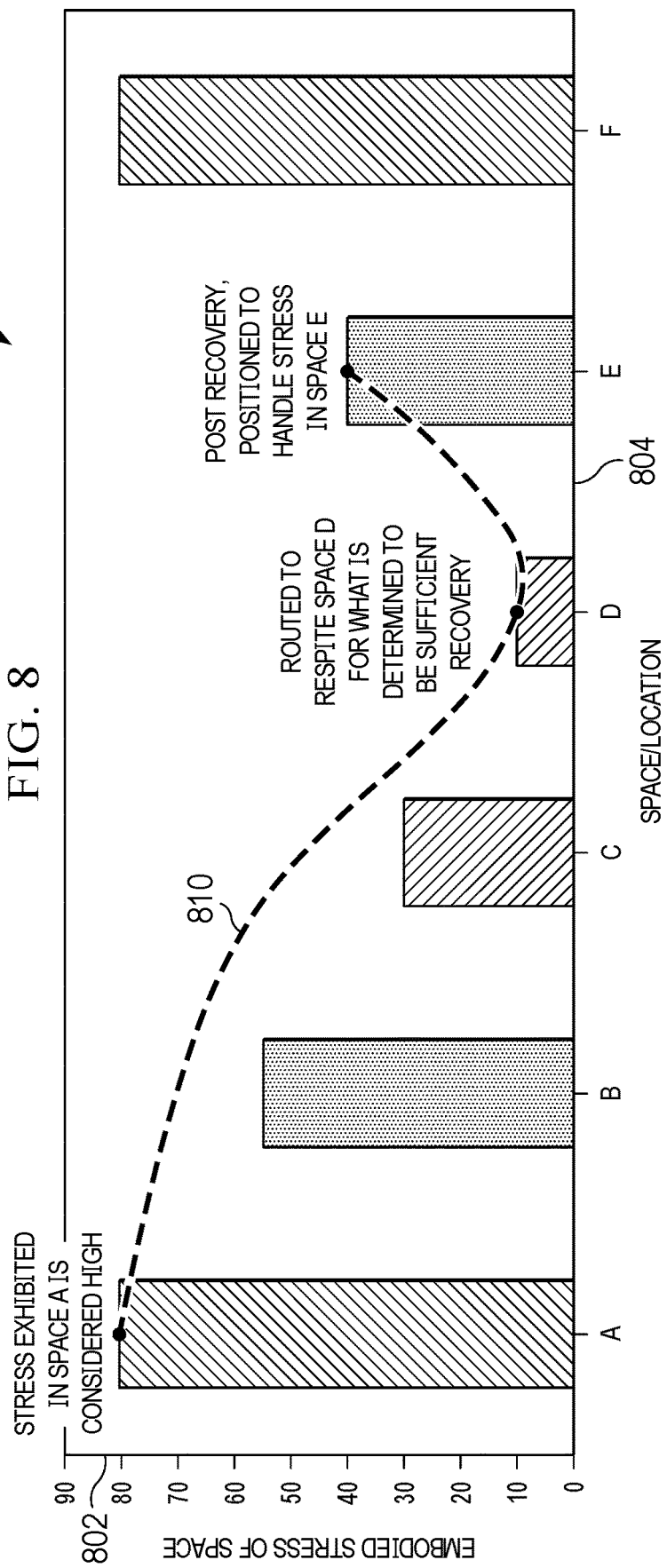
FIG. 8 illustrates an embodied stress of location chart, according to an embodiment.

FIG. 8 illustrates embodied stress of location chart 800, according to an embodiment. Stress of location chart 800 comprises embodied stress of space 802 on the x-axis and space/location 804 on the y-axis. As an example only and not by way of limitation, a stress journey 810 starts in Space A (depicted in Column A), which depicts a very high user stress exhibited. That user then is routed to respite Space C (depicted in Column C), where we observe very low user stress. The user then is routed to Space E (depicted in Column E) where the user might be in a very high stress area or function, but there relative stress is lower because they have spent time in Space C just prior.

Figure 9:
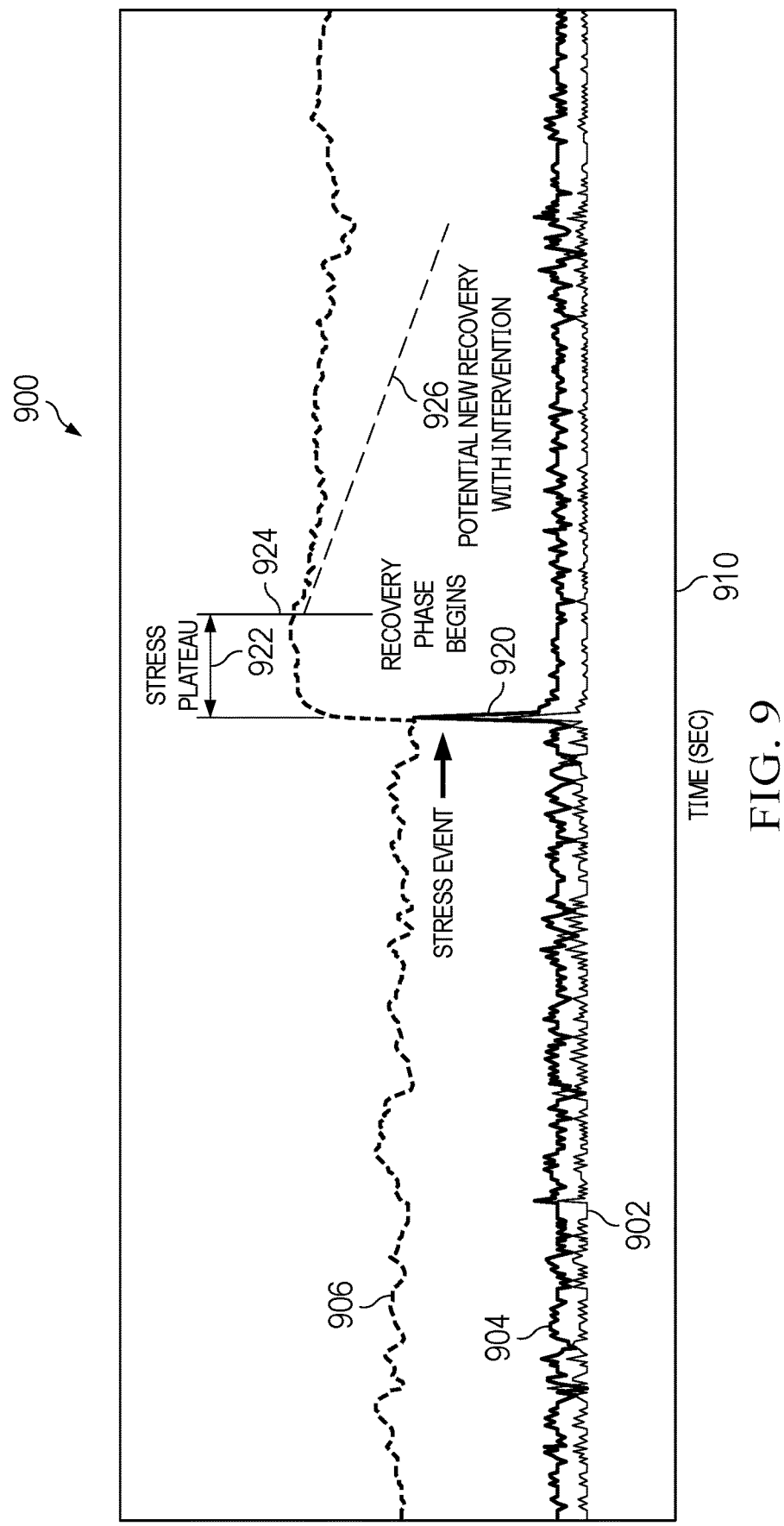
FIG. 9 illustrates a stress timeline and recovery chart, according to an embodiment.

FIG. 9 illustrates stress timeline and recovery chart 900, according to an embodiment. Stress timeline and recovery chart 900 comprises line 906 representing raw heart rate, line 904 which represents output from our stress algorithm, and line 902 which is the historic calculation of heart-rate variability. According to embodiments, stress timeline and recovery chart 900 further comprises stress event 920, stress plateau 922, recovery phase begins 924 and potential new recovery with intervention 926.

Embodiments contemplate embodied stress analyzer 110 algorithmically detecting flow state and/or recovery. In some embodiments, embodied stress analyzer 110 detects flow state and/or recovery of a locational context, such as, for example, a park, a street, a construction zone, a medical facility, or the like. In addition, or as an alternative, embodied stress analyzer 110 detects flow state and/or recovery of an individual. According to embodiments, embodied stress analysis system 110 and embodied stress analysis method 300 may utilize data collected according to biometric feedback method 1000, according to particular needs and as described in further detail below.

Figure 10:
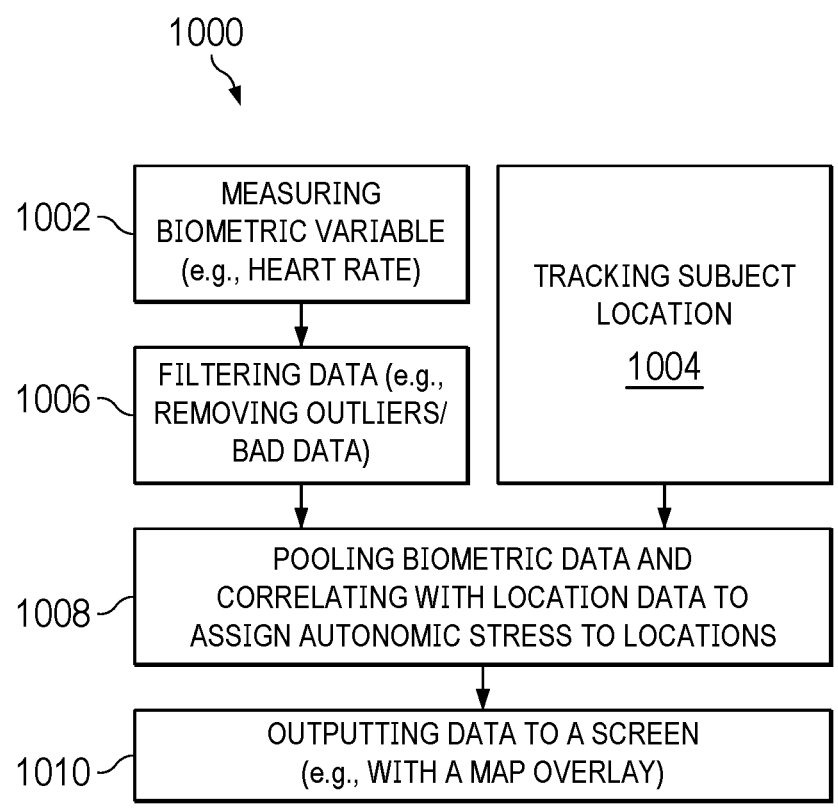
FIG. 10 illustrates an exemplary biometric feedback method, according to an embodiment.

FIG. 10 illustrates an exemplary biometric feedback method 1000, according to an embodiment. Biometric feedback method 1000 proceeds by one or more activities, which although described in a particular order may be performed in one or more permutations, combinations, orders, or repetitions, according to particular needs. A flow diagram illustrating exemplary operation of the biometric feedback method is included in FIG. 10 with activities 1002, 1004, 1006, 1008, and 1010, as indicated.

In emotionally stressful situations, the Sympathetic Nervous System automatically accelerates the production of adrenaline, leading to an immediate and involuntary increase in blood and oxygen flows to the brain and muscles. This is called an autonomic response, a form of emotional stress, which is different (and measurably distinguishable) from physical stress. In the following examples, biometric feedback method 1000 focused on autonomic (emotional) stress (not physical stress) and how factors in the built environment impacted autonomic responses. Embodiments contemplate including, or filtering out, autonomic emotional states that may be described as either good stress (known as eustress—e.g., the thrill of competition) or bad stress (known as distress—e.g., the sense of inability to control stimuli in one's environment), according to particular needs.

The presence or absence of autonomic stress can be detected and measured by analyzing heart rate data. Most consumer-grade fitness sensors capture heart rate data (measured in beats per minute) over a period of time. According to an embodiment, the biometric feedback method 1000 isolates emotionally-induced stress by filtering out physically-induced stress. This may be done by calculating the individual's baseline heart rate, and applying a mathematical analytical algorithm as described above.

Figure 11:
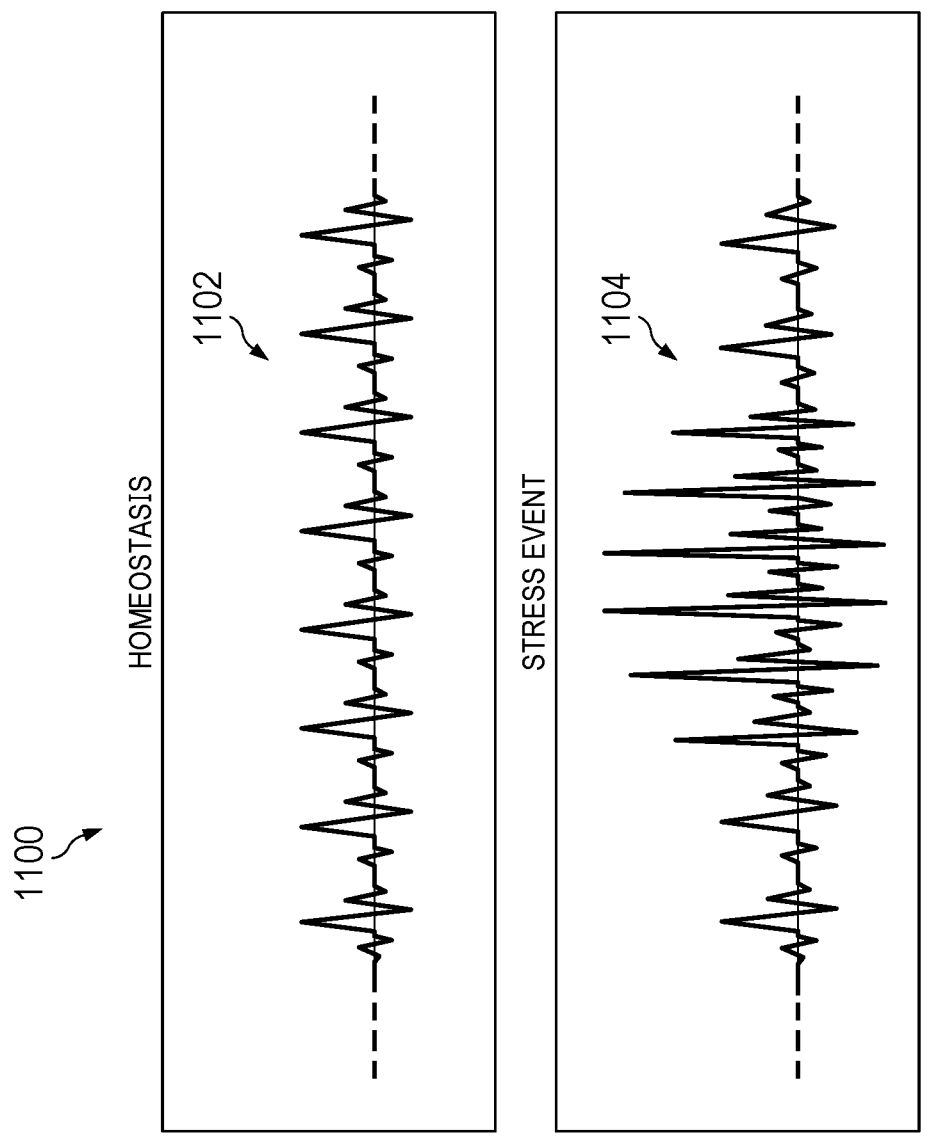
FIG. 11 illustrates an of heart rate variability of a subject when in homeostasis and when subjected to a stress event, according to an embodiment.

FIG. 11 illustrates homeostasis and a stress event chart 1100, according to an embodiment. According to embodiments, homeostasis and a stress event chart 1100 illustrates an exemplary heart rate variability of a subject when in homeostasis and when subjected to a stress event, wherein upper chart 1102 is homeostasis and lower chart 1104 is a stress event.

Figure 12:
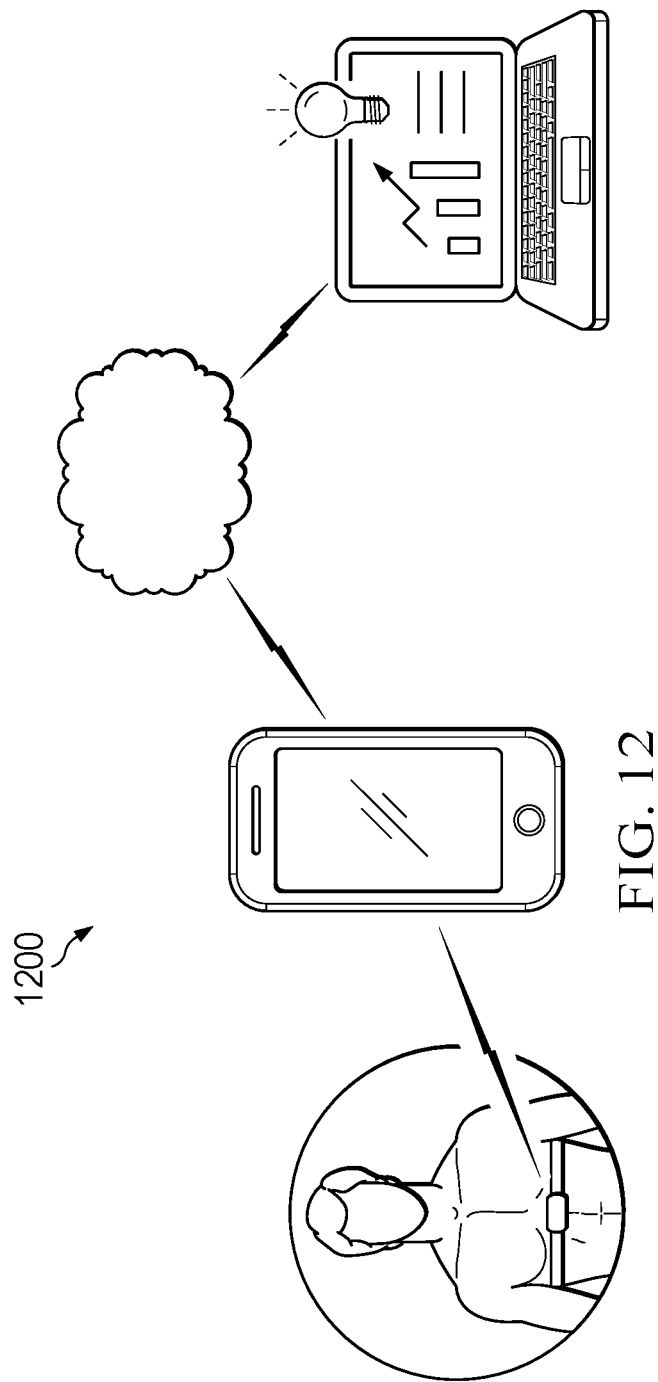
FIG. 12 illustrates an exemplary biometric feedback system, according to an embodiment.

FIG. 12 illustrates exemplary biometric feedback system 1200, according to an embodiment. Embodiments provide for digital linkages to move heartrate data from chest strap sensors to the fitness app on a smart phone and then to the fitness app's cloud server. In addition, embodiments access the data from the fitness app's cloud via an application programming interface (API). If the study involves multiple users/subjects (i.e., a sample size greater than 1), the "Stress Score" can also be compared across multiple users/subjects and further averaged to better identify outliers for specific users/subjects and establish broader patterns of stress for a larger userbase. In other words, if the study involves several users/research subjects and locations A and B, the Stress Scores for each user at the same location can be averaged (with or without removing outliers) to develop an average user Stress Score for location A and an average user Stress Score for location B.

Figure 13:
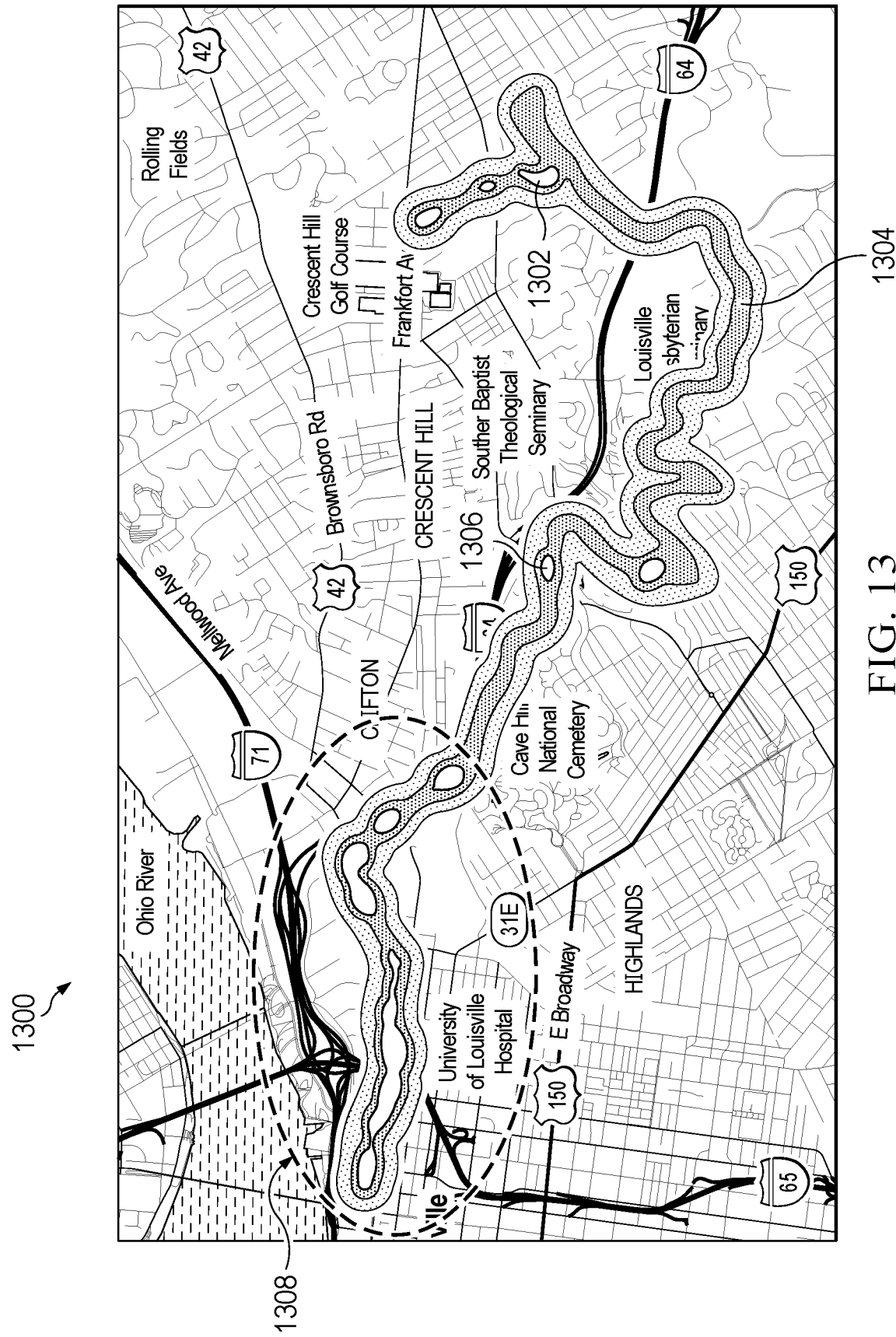
FIG. 13 illustrates a heatmap visualization of an exemplary commute route, according to an embodiment.

FIG. 13 illustrates a heatmap visualization 1300 of an exemplary commute route, according to an embodiment. Heat map visualization 1300 highlights locations of elevated autonomic stress where elevated stress is shown in lighter shading utilizing data logged by a staff member on his daily bicycle commutes to and from the office. Many of these locations are at street intersections requiring negotiations with vehicles, which happened more frequently near the city center. More interestingly, "hot spots" emerged that coincided with the memories of a repaired pothole and an accident along otherwise relatively calm stretches of the commute. For example, at location 1302 the location of a former pothole still created stress even after the pothole was repaired. The lowest stress was recorded at location 1304 where there is an abundance of green space and a lack of conflicts. At location 1306, the memory of a collision with a car six months ago still creates a successful event at the location of the accident. In the city center, location 1308, the stress levels are higher even though the terrain is flatter because the environment is not very user-friendly.

Figure 14:
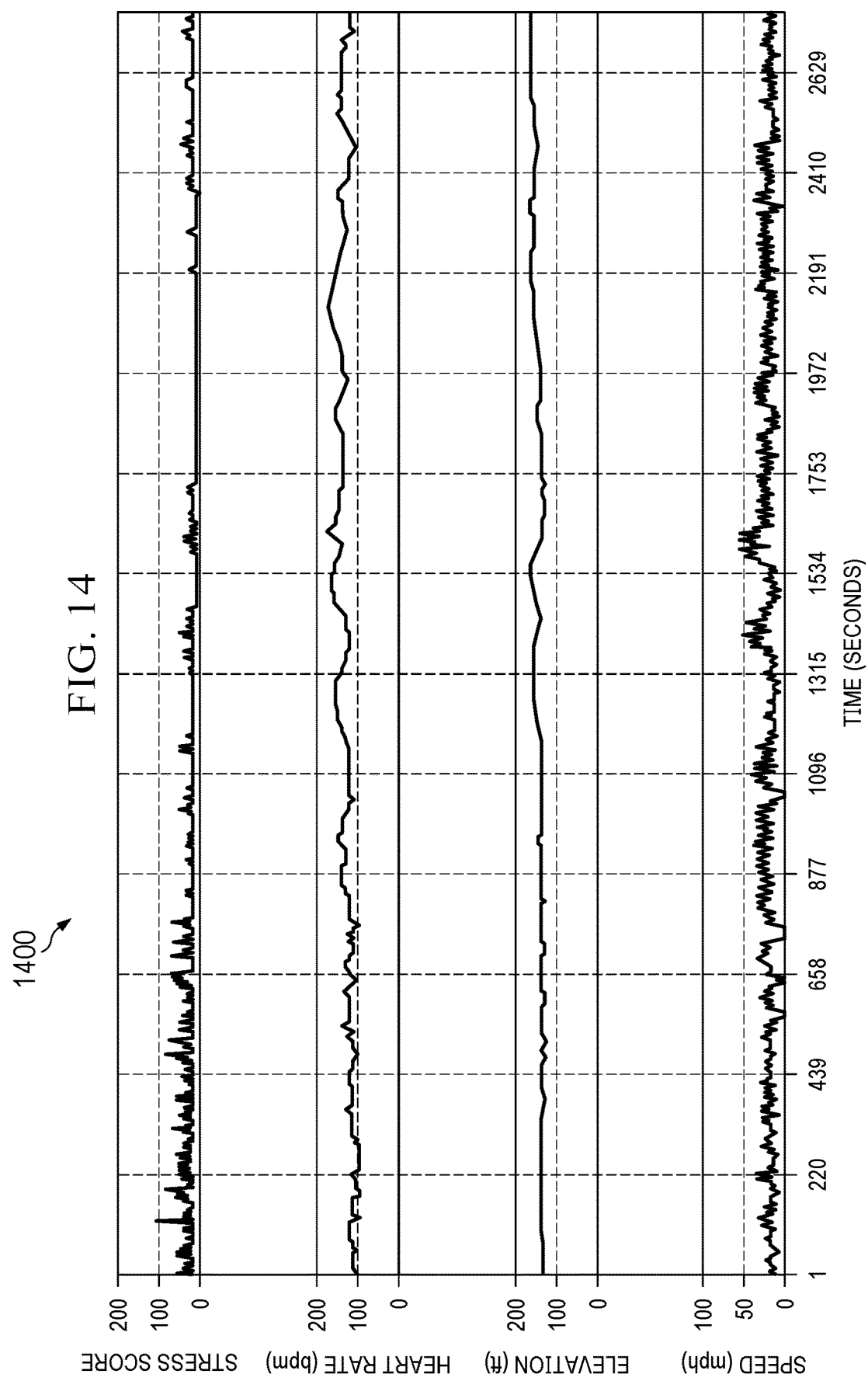
FIG. 14 illustrates exemplary stress charts, according to an embodiment.

FIG. 14 illustrates exemplary stress charts 1400, according to an embodiment. Stress charts 1400 indicate measurements of stress may not correlate to physical exertion stressors. The Stress chart is the result of the heart rate fluctuations analysis of the heart rate data. Elevation ascents seem to show some correlation to increases in heart rate while descents correlate to increases in speed. However, the autonomic stress metrics in these locations seem relatively stable which points to successful measurements of autonomic stress based on the context at that location after removal of stress attributable to physical exertion. Conversely, the early stages of the route (in the city center) are on relatively flat terrain but show the highest amounts of autonomic stress. Also, the highest heart rates—all recorded in the second half of the commute—correlate to the lowest autonomic stress levels. Thus, it was observed that the platform was successfully isolating emotional (autonomic) stress from physical stress. The horizontal axis in the charts below refers to time (in seconds from start). In the top graph, the vertical axis refers to the stress score (the stress score being a normalized value provided on a scale of 0-100 of the measurement of the stress response). In the heart rate chart, the vertical axis refers to heart rate in beats per minute. In the elevation chart, the vertical axis refers to elevation above sea level in feet. In the speed chart, the vertical axis refers to speed in miles per hour.

Biometric feedback method 1000 may be further applied to redesign of the Eastern Parkway in Louisville, Ky. There were a number of pre-design strategies employed to collect information and data, including: 1) an online survey which gathered information from the public about their opinions and impressions of the Parkway; 2) a town-hall-style public forum in which the community could interact with the design team about the Parkway; 3) a walking workshop tour of the Parkway with about 20 members of the group, in which they were able to record answers on iPad surveys at specific points along the Parkway walk; and 4) analysis of various types of third-party data, for example, vehicle crash data. During the "walking workshop" on the Parkway, a small number of users wore chest straps to capture their heart rate data.

Figure 15:
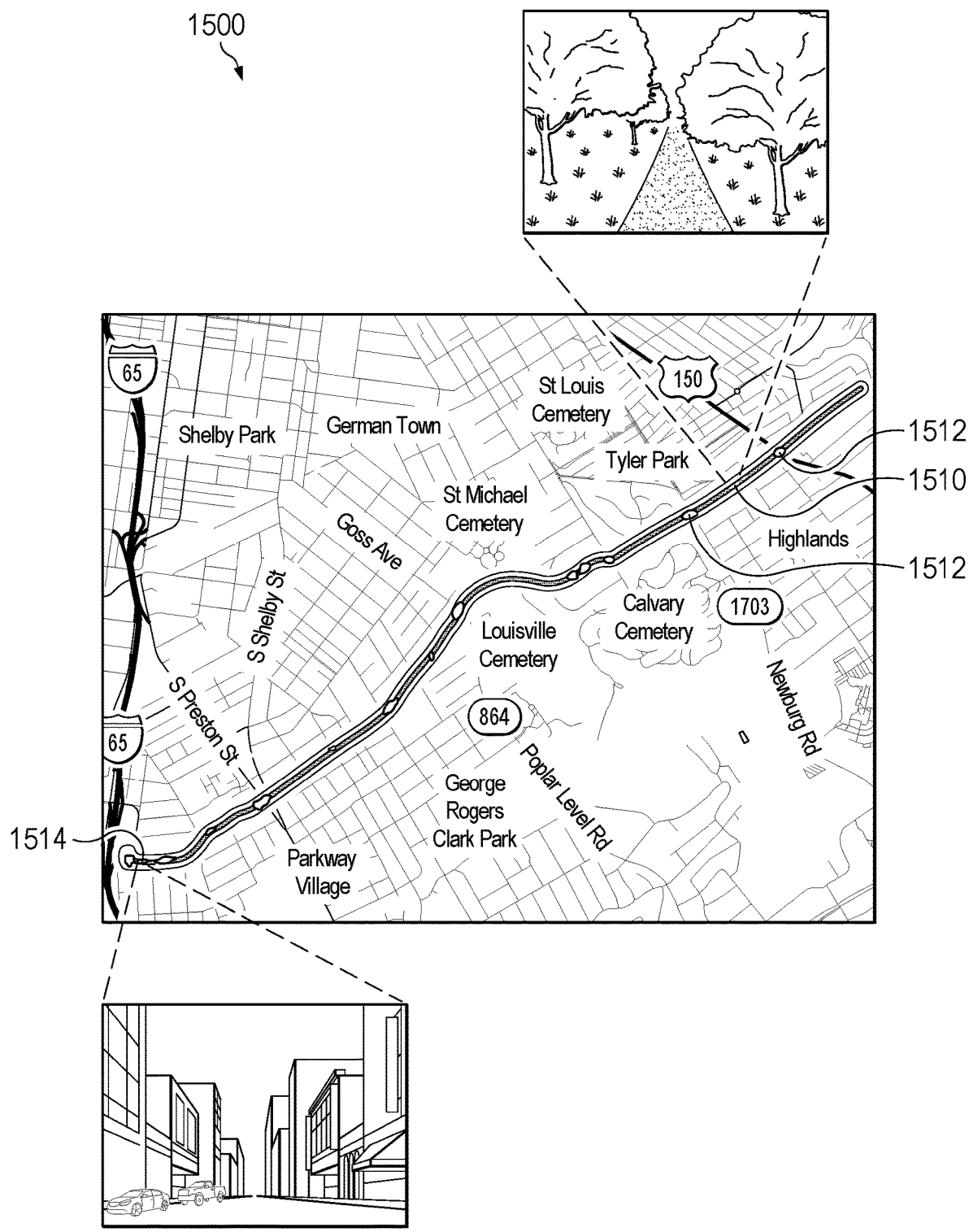
FIG. 15 illustrates an exemplary heat map visualization, according to an embodiment.

FIG. 15 illustrates "Parkway" heat map visualization 1500, according to an embodiment. "Parkway" heat map visualization 1500 indicates lower stress levels associated with locations where: 1) the sidewalks are further away from the street, or shielded from the street with natural vegetation; and 2) there are heavier tree canopies with mature trees. Conversely, higher stress was associated with locations where: 1) the sidewalks are closer to the street; and 2) there were highly active street intersections and the crossing durations were longer. More particularly, at location 1510, some of the lowest levels of stress were located in the areas with abundant landscaping and good separation from vehicles. A favorite section of the parkway is bounded by very stressful access points 1512 where it is necessary to cross traffic to get to the sidewalk in the median. The western terminus 1514 of the Parkway merges with a major thoroughfare, with minimal consideration given to pedestrian experience, resulting in very high stress levels.

The stress data appeared to be well-aligned with the other datasets that were collected. Correlation with the crash data was especially interesting, seeing that locations of the highest crash counts coincided with some of the highest recorded stress levels, even in the absence of any actual crash events during the workshop.

According to embodiments, the method for deriving autonomic stress from heart rate variability data provided a useful tool to assess the level of latent stress in a physical environment. In addition, or as an alternative, biometric feedback method maps which ambient settings cause stress and quantifies settings that lead to lower stress and homeostasis. This analysis provides quantifiable data for phenomena that have only been qualifiable up to this point.

According to embodiments, an example of a subject/user using the biometric feedback method follows. The subject begins by recording location and heart rate as the subject moves around outdoor or indoors. The subject walks, bikes, or rides in a car around town or in public space. Alternatively, the subject may move about an indoor space, such as a building. The subjects, for example, may feed the data to the software platform or alternatively the software platform may, for example, automatically retrieve the data. The platform may remove outliers (any bad data where the heart rate monitor may disconnect from the user). The platform may remove duplicate location data (optional, but used where a subject stands still at a certain location for an extended amount of time and forgets to pause his/her recording). The platform may convert the heart rate to heart rate variability. The platform may normalize and average readings across multiple subjects (if multiple subjects are present). The platform may export location data coupled with a stress score which can be plotted on, for example, a map.

In some embodiments, the present disclosure provides a biometric feedback method of ascertaining biometric stress to an environmental condition comprising: activity a: using a plurality of biometric sensors (e.g., at least one sensor worn by each subject) to collect biometric data (e.g., heart rate, heart rate variability, blood pressure, oxygenation, galvanic response, facial sentiment analysis, and/or eye movement) over time from a plurality of subjects while the subjects move about a plurality of locations; activity b: using a plurality of location sensors to track the locations of the plurality of subjects over time while the subjects move about the plurality of locations, at least some of said subjects moving about at least partially overlapping locations (e.g., coming within five feet of the same location so that each location has readings from more than one subject); and activity c: grouping/segregating/sorting the biometric data, with or without filtering the data, by location (e.g., to assign a biometric score to each location).

In addition to, or as an alternative, the biometric method may comprise one or more of the following embodiments: (1) biometric data comprises heart rate data of the respective subjects over time; (2) the biometric feedback method further comprises the activity of filtering out physically-induced stress (so that the system only measures autonomic stress for each location); (3) the activity of filtering out physically-induced stress occurs prior to grouping/segregating/sorting the biometric data by location; (4) the biometric data collected in activity a comprises the heart rate data of the respective subjects over time and wherein the method further comprises applying an algorithm to the biometric data to calculate heart rate variability over time for the respective subjects (e.g., by calculating the baseline heart rate of each respective subject within the plurality of subjects and applying the root mean square of the successive differences to the biometric data); (5) activity c further comprises displaying the biometric data segregated/sorted by location on an electronic screen (e.g., a computer screen); (6) activity c further comprises displaying the biometric data segregated/sorted by location and a map on an electronic screen; (7) using the biometric feedback system in an outdoor or indoor environment (thus, the term "map" as used herein includes, for example, reference maps as well as floorplans); (8) the biometric feedback method further comprises the activity of filtering the biometric data (e.g., to remove occasions where the user was standing still or the sensor fell off the subject); (9) the biometric data comprises data about one or more of heart rate, heart rate variability, blood pressure, oxygenation, galvanic response, facial sentiment analysis, and/or eye movement, etc.; (10) the biometric sensor and the location sensor are located on a wearable (e.g., watch or other wrist strap, arm band, chest strap, etc.); (11) the biometric method further comprises activity d: assigning a biometric stress score to each of the plurality of locations; (12) the biometric sensor comprises a chest strap, arm band, watch or other wrist strap or other wearable configured to measure the subjects' heart rates; (13) the location sensor is a GPS tracker, indoor positioning system, or a device that employs other location based techniques; (14) the biometric method further comprises using one or more power sources (e.g., a battery) to power the location sensor and the biometric sensor and the location sensor and biometric sensor are electronic; (15) the biometric method further comprises activity e: altering the environment at a location (e.g., adding trees, a sidewalk, adding width to a street, modifying architectural details, installing art, rearranging furniture, or changing lighting in response to a high stress reading); (16) two or more biometric sensors comprise two or more heart rate monitors; (17) two or more biometric sensors and the two or more location sensors may be located in different devices; (18) these different devices also record temporal data along with the biometric data or location data; (19) temporal data may be used to group/associate the biometric data with the corresponding location data at the same time interval; (20) a GPS unit may record a subject's location at time 1, and a wearable device worn by a user may record the subject's heart rate at time 1; (21) the biometric data and location data may be merged, and the location at time 1 and the heart rate at time 1 may be grouped together.

In still further embodiments, the present disclosure provides a method of assigning autonomic stress to a location comprising: a) using a plurality of heart rate monitors to collect heart rate data from a plurality of subjects over time while the subjects move about a plurality of locations, each subject wearing a heart rate monitor; b) using a plurality of location sensors to track the location of the plurality of subjects over time while the subjects move about the plurality of locations, at least some of said subjects at least partially overlapping locations; c) applying an algorithm to the heart rate data for each subject to determine heart rate variability for each subject; and d) grouping/segregating/sorting heart rate variability by location. In addition, or as an alternative, this method further comprises displaying said heart rate variability for each location on an electronic screen; and/or displaying said heart rate variability for each location together with a map on an electronic screen.

In still further embodiments, the present disclosure provides a method of assigning autonomic stress to a location comprising: a) using a plurality of heart rate monitors to collect heart rate data from a plurality of subjects over time while the subjects move about a plurality of locations, each subject wearing a heart rate monitor; b) using a plurality of location sensors to track the location of the plurality of subjects over time while the subjects move about the plurality of locations, at least some of said subjects at least partially overlapping locations; c) filtering out physically-induced stress in the heart rate data, said activity of filtering out physically induced stress comprising calculating each subject's baseline heart rate and applying an algorithm comprising root mean square of the successive differences to the heart rate data; and d) grouping/segregating/sorting the filtered heart rate data by location.

Optionally, the method further comprises: e) after activity d), displaying on an electronic screen autonomic stress levels for each of the plurality of locations.

In still further embodiments, the present disclosure provides a method of assigning autonomic stress to a location comprising: a) using a plurality of heart rate monitors to collect heart rate data from a plurality of subjects over time while the subjects move about a plurality of locations, each subject wearing a heart rate monitor; b) using a plurality of location sensors to track the location of the plurality of subjects over time while the subjects move about the plurality of locations, at least some of said subjects move about at least partially overlapping locations; c) grouping/segregating/sorting the heart rate data based on location and filtering out physically-induced stress from the heart rate data, said activity of filtering out physically-induced stress comprising calculating each subject's heart rate variability and applying an algorithm comprising root mean square of the successive differences to the heart rate data; and d) displaying on an electronic display screen autonomic stress levels for the plurality of locations based, at least in part, on activity c).

In still further embodiments, the present disclosure provides a method of assigning a biometric stress score to a location comprising: a) using at least one biometric sensor and at least one location sensor to simultaneously collect biometric data and location data for at least one subject over time as the at least one subject moves about a plurality of locations; and b) using the biometric data and the location data, with or without filtering the biometric data, to assign a biometric stress score to some or all of the plurality of locations.

Optionally, in activity b), the biometric data is filtered to remove physical-induced stress. Optionally, the method further comprises the activity of displaying the biometric stress scores on an electronic screen (e.g., optionally with a map).

In still further embodiments, the present disclosure provides a method of assigning autonomic stress to a location comprising: a) using a plurality of heart rate monitors and a plurality of location sensors to simultaneously collect heart rate data and location data for a plurality of subjects over time as the plurality of subjects move about a plurality of locations, each subject wearing a heart rate monitor; b) processing the heart rate data and the location data of each subject to assign a biometric stress score to some or all of the plurality of locations for each subject; and c) for each location, combining (e.g., averaging with or without removing outliers) the subject-level biometric stress scores to determine a cumulative biometric stress score for each location.

Optionally, the method further comprises the activity of displaying the cumulative biometric stress scores on an electronic screen (e.g., optionally with a map). Optionally, activity b) comprises applying an algorithm comprising root mean square of the successive differences to the heart rate data to filter out physically-induced stress.

In still further embodiments, the present disclosure provides a method of ascertaining biometric stress to an environmental condition comprising: a) presenting images of different locations or interactive 3D models on an electronic display to one or more subjects through virtual or augmented reality over time (e.g., through a head-mounted display worn by the subjects); b) using a plurality of biometric sensors to collect biometric data (e.g., heart rate, heart rate variability, blood pressure, oxygenation, galvanic response, facial sentiment analysis, and/or eye movement) over time from the one or more subjects while the subjects are presented the images; and c) grouping/segregating/sorting the biometric data, with or without filtering the data, by location (e.g., to assign a biometric score to each presented location).

Reference in the foregoing specification to "one embodiment", "an embodiment", or "another embodiment" means that a particular feature, structure, or characteristic described in connection with the embodiment is included in at least one embodiment of the invention. The appearances of the phrase "in one embodiment" in various places in the specification are not necessarily all referring to the same embodiment.

While the exemplary embodiments have been shown and described, it will be understood that various changes and modifications to the foregoing embodiments may become apparent to those skilled in the art without departing from the spirit and scope of the present invention.

What is claimed is:

1. A method of measuring embodied stress relative to a location comprising:

receiving, by a computer comprising a processor and memory, stress measurement data from one or more sensors of one or more stress monitoring devices;

building, by the computer, a locational model from mapping data;

receiving, by the computer, location data for the one or more stress monitoring devices, wherein the location data is correlated with the stress measurement data;

filtering, by the computer, the stress measurement data and the location data by comparing the location data to a locational model;

aggregating, by the computer, the filtered stress measurement data and the filtered location data into groups according to one or more bins, wherein the one or more bins are defined by a grid;

analyzing, by the computer, the stress measurement data and the location data to associate the stress measurement data with the location data according to the locational model;

generating, by the computer, a stress visualization based on the stress measurement data and the location data; and deriving, by the computer, an emotion of one or more locations according to the locational model.

2. The method of claim 1, wherein the stress measurement data and the location data are filtered by a role of a user corresponding to the stress measurement data and the location data.

3. The method of claim 1, wherein the analyzing further comprises:

aggregating, by the computer, individual stress scores according to the locational model;

binning, by the computer, the aggregated individual stress scores based on locational boundary conditions according to locations within the locational model; and normalizing, by the computer, the aggregated binned data to determine a particular score for each of the locations defined by the locational model.

4. The method of claim 1, wherein the method further comprises:

performing, by the computer, a locational sequence analysis by tracking changes in the aggregated individual stress scores along a sequence of locations within the locational model; and generating, by the computer, a visualization of the locational sequence analysis.

5. The method of claim 4, wherein the method further comprises:

planning, by the computer, a sequence of locations based on the locational sequence analysis to cause a reduction in aggregated individual stress scores.

6. The method of claim 1, wherein the stress management data is heartrate stress data determined by a low-polling algorithm.

7. The method of claim 6, wherein the low polling algorithm is based on a slope analysis and a rate of change comparison of heartrate.

8. A system for measuring embodied stress relative to a location comprising:
a computer comprising a memory and a processor and configured to:
receive stress measurement data from one or more sensors of one or more stress monitoring devices;
build a locational model from mapping data;
receive location data for the one or more stress monitoring devices, wherein the location data is correlated with the stress measurement data;
filter the stress measurement data and the location data by comparing the location data to a locational model;
aggregate the filtered stress measurement data and the filtered location data into groups according to one or more bins, wherein the one or more bins are defined by a grid;
analyze the stress measurement data and the location data to associate the stress measurement data with the location data according to the locational model;
generate a stress visualization based on the stress measurement data and the location data; and
derive an emotion of one or more locations according to the locational model.

9. The system of claim 8, wherein the stress measurement data and the location data are filtered by a role of a user corresponding to the stress measurement data and the location data.

10. The system of claim 8, wherein the computer is further configured to perform the analyzing by:
aggregate individual stress scores according to the locational model;
bin the aggregated individual stress scores based on locational boundary conditions according to locations within the locational model; and
normalize the aggregated binned data to determine a particular score for each of the locations defined by the locational model.

11. The system of claim 8, wherein the computer is further configured to:
perform a locational sequence analysis by tracking changes in the aggregated individual stress scores along a sequence of locations within the locational model; and
generate a visualization of the locational sequence analysis.

12. The system of claim 11, wherein the computer is further configured to:
plan a sequence of locations based on the locational sequence analysis to cause a reduction in aggregated individual stress scores.

13. The system of claim 8, wherein the stress management data is heartrate stress data determined by a low-polling algorithm.

14. The system of claim 13, wherein the low polling algorithm is based on a slope analysis and a rate of change comparison of heartrate.

15. A non-transitory computer-readable medium embodied with software for measuring embodied stress relative to a location, the software when executed:
receives stress measurement data from one or more sensors of one or more stress monitoring devices;
builds a locational model from mapping data;
receives location data for the one or more stress monitoring devices, wherein the location data is correlated with the stress measurement data;
filters the stress measurement data and the location data by comparing the location data to a locational model;
aggregates the filtered stress measurement data and the filtered location data into groups according to one or more bins, wherein the one or more bins are defined by a grid;
analyzes the stress measurement data and the location data to associate the stress measurement data with the location data according to the locational model;
generates a stress visualization based on the stress measurement data and the location data; and
derives an emotion of one or more locations according to the locational model.

16. The non-transitory computer-readable medium of claim 15, wherein the stress measurement data and the location data are filtered by a role of a user corresponding to the stress measurement data and the location data.

17. The non-transitory computer-readable medium of claim 15, wherein the software when executed further:
aggregates individual stress scores according to the locational model;
bins the aggregated individual stress scores based on locational boundary conditions according to locations within the locational model; and
normalizes the aggregated binned data to determine a particular score for each of the locations defined by the locational model.

18. The non-transitory computer-readable medium of claim 15, wherein the software when executed further:
performs a locational sequence analysis by tracking changes in the aggregated individual stress scores along a sequence of locations within the locational model; and
generates a visualization of the locational sequence analysis.

19. The non-transitory computer-readable medium of claim 18, wherein the software when executed further:
plans a sequence of locations based on the locational sequence analysis to cause a reduction in aggregated individual stress scores.

20. The non-transitory computer-readable medium of claim 15, wherein the stress management data is heartrate stress data determined by a low-polling algorithm based on a slope analysis and a rate of change comparison of heartrate.

* * * * *